US007678834B2

(12) United States Patent
Sundermann et al.

(10) Patent No.: US 7,678,834 B2
(45) Date of Patent: *Mar. 16, 2010

(54) SUBSTITUTED 4-AMINOCYCLOHEXANOL COMPOUNDS

(75) Inventors: Bernd Sundermann, Aachen (DE); Hagen-Heinrich Hennies, Simmerath (DE); Babette-Yvonne Koegel, Langerwehe (DE); Stephan Wnendt, Aachen (DE)

(73) Assignee: Gruenenthal GmbH, Aachen (DE)

( * ) Notice: Subject to any disclaimer, the term of this patent is extended or adjusted under 35 U.S.C. 154(b) by 1571 days.

This patent is subject to a terminal disclaimer.

(21) Appl. No.: 10/758,241

(22) Filed: Jan. 16, 2004

(65) Prior Publication Data

US 2004/0214822 A1    Oct. 28, 2004

Related U.S. Application Data

(63) Continuation of application No. PCT/EP02/07849, filed on Jul. 15, 2002.

(30) Foreign Application Priority Data

Jul. 17, 2001  (DE)  ............................... 101 35 635
Jul. 17, 2001  (DE)  ............................... 101 35 637

(51) Int. Cl.
*A01N 31/00* (2006.01)
*A01N 43/78* (2006.01)
*A61K 31/405* (2006.01)
*C07C 211/00* (2006.01)
*C07D 277/62* (2006.01)

(52) U.S. Cl. ...................... 514/724; 514/367; 514/415; 548/179; 564/307

(58) Field of Classification Search ................. 514/724, 514/367, 415; 567/307; 548/179
See application file for complete search history.

(56) References Cited

U.S. PATENT DOCUMENTS

| 4,115,589 | A | 9/1978 | Lednicer |
| 4,212,878 | A | 7/1980 | Lednicer et al. |
| 4,346,101 | A | 8/1982 | Lednicer |
| 4,366,172 | A | 12/1982 | Lednicer |
| 4,777,986 | A | 10/1988 | Brochier |
| 5,239,110 | A | 8/1993 | Mallamo et al. |
| 5,304,479 | A | 4/1994 | Lin |
| 5,309,950 | A | 5/1994 | Bassi et al. |
| 6,495,565 | B2 | 12/2002 | Duan et al. |
| 7,183,436 | B2 * | 2/2007 | Sundermann et al. ....... 564/307 |

FOREIGN PATENT DOCUMENTS

| DE | 160007 | 5/1903 |
| DE | 2839891 | 4/1979 |
| DE | 19963175 | 7/2001 |
| DE | 20118363 | 2/2002 |
| EP | 0410191 | 1/1991 |
| EP | 0472904 | 3/1992 |
| FR | 2135883 | 12/1972 |
| FR | 2726011 | 4/1996 |
| WO | WO 01/12195 | 2/2001 |
| WO | WO 01/70734 A2 | 9/2001 |

OTHER PUBLICATIONS

Pain, http://www.medterms.com/script/main/art.asp?articlekey=4723, 3 pages.*
Zeller et al. Acute Pain Treatment, JAMA, 299(1):128-129, 2008.*
Drakontides, Drugs to Treat Pain, American Journal of Nursing,pp. 508-513, Mar. 1974.*
Ossipov et al., Challenges in the Development of Novel Treatment Strategies for neuropathic pain, The Journal of the American Society for Experimental NeuroTherapeutics, 2(4), 650-661, 2005.*
Bannon et al, Models of Nocioception: Hot-plate, tail-Flick, and Formalin tests in Rodents, Current Protocols in Neuroscience, 8.9.1-8.9.16, 2007.*
Griffiths et al., Emerging and potential therapies for Alzheimer's disease, Expert Opinion of Therapeutic Targets, 12(6): 693-704, 2008.*
Abstract, Velisek et al., New avenue of research: antieliptic drug and estradiol neuroprotection in epilepsy, 3(2):128-37, 2008.*
DeRubeis et al. Cognitive therapy versus medication for depression: treatment outcomes and neural mechanism, Nature Reviews, vol. 9, pp. 788-796 2008.*
Driscoll et al, Medical therapy for pulmonary arterial hypertension, Expert Opinion on Pharmacotherapy, 9(1):65-81, 2008.*
Zandian et al., Cause and treatment of anorexia nervosa, Physiology & Behavior, vol. 92 p. 283-290, 2007.*
Pain, http://www.medterms.com/script/main/art.asp?articlekey=4723, 3 pages. 2008.*
R. Chou, et al, "Clinical Guidelines for the Use of Chronic Opioid Therapy in Chronic Noncancer Pain", The Journal of Pain, vol. 10, No. 2, Feb. 2009, pp. 113-130.
E. Eisenberg, et al, Opioids for Neuropathic Pain (Review), Cochrane Database of Systematic Reviews 2006, Issue 3, Art. No. CD006146. DOI: 10.1002/14651858.CD006146.
Daniel Lednicer et al., "4-(p-Bromophenyl)-4-(dimethylamino)-1-phenethylcyclohexanol, an Extremely Potent Representative of a New Analgesic Series", Journal of Medicinal Chemistry, Oct. 1979, pp. 1157-1158, vol. 22, No. 10, American Chemical Society.
Hiroshi Kawamoto et al., "Synthesis of J-113397, the First Potent and Selective ORL1 Antagonist," Tetrahedron, 2001, pp. 981-986, 57, Elsevier Science Ltd.
Daniel Lednicer et al., "4-Aryl-4-aminocyclohexanones and Their Derivatives, a Novel Class of Analgesics," Journal of Medicinal Chemistry, 1981, pp. 341-346, vol. 24, No. 3, American Chemical Society.

(Continued)

*Primary Examiner*—Johann R Richter
*Assistant Examiner*—Kristie L Brooks
(74) *Attorney, Agent, or Firm*—Crowell & Moring LLP

(57) ABSTRACT

4-aminocyclohexanol compounds, processes for their preparation, pharmaceutical formulations comprising these compounds and the use of substituted 4-aminocyclohexanol compounds for the preparation of pharmaceutical formulations and for the treatment of diverse indications, including, without limitation, pain.

51 Claims, No Drawings

OTHER PUBLICATIONS

Daniel Lednicer et al., "4-Amino-4-arylcyclohexanones and Their Derivatives: A Novel Class of Analgesics," Journal of Medicinal Chemistry, 1981, pp. 404-408, vol. 24, No. 4, American Chemical Society.

Faud A. Abdulla et al., "Axotomy Reduces the Effect of Analgesic Opioids Yet Increases the Effect of Nociceptin on Dorsal Root Ganglion Neurons," The Journal of Neuroscience, Dec. 1, 1998, pp. 9685-9694, 18, 23, Society for Neuroscience.

Girolamo Calo et al., "Pharmacology of Nociceptin and its Receptor: A Novel Therapeutic Target," British Journal of Pharmacology, 2000, pp. 1261-1283, 129, Macmillan Publishers Ltd.

Mark Conner et al., "The Effect of Nociceptin on $Ca^{2+}$ Channel Current and Intracellular $Ca^{2+}$ in the SH-SY5Y Human Neuroblastoma Cell Line", 1996, pp. 205-207, 118, Stockton Press.

E.S.L. Faber et al., "Depression of Glutamatergic Transmission by Nociceptin in the Neonatal Rat Hemisected Spinal Cord Preparation In Vitro", Special Report, Jul. 19, 1996, pp. 1-2.

"Opioid and Opiate Receptors: Peptides and Knock-Out," Society for Neuroscience, 1998, p. 1358, vol. 24.

Francois Jenck et al., "Orphanin FQ Acts as an Anxiolytic to Attenuate Behavioral Responses to Stress," Proc. Natl. Acad. Sci., Dec. 1997, pp. 14854-14858, vol. 94, USA.

Michael A. King et al., "Spinal Analgesic Activity of Orphanin FQ/Nociceptin and its Fragments", Neuroscience Letters, 1997, pp. 113-116, 223, Elsevier Science Ireland Ltd.

Toshiya Manabe et al., "Facilitation of Long-Term Potentiation and Memory in Mice Lacking Nociceptin Receptors", Letters To Nature, Aug. 6, 1998, pp. 577-581, vol. 394, Macmillan Publishers Ltd.

Jean-Claude Meunier et al., "Isolation and Structure of the Endogenous Agonist of Opiod Receptor-Like $ORL_1$ Receptor," Letters to Nature, Oct. 12, 1995, pp. 532-535, vol. 377.

J.S. Mogil et al., "Orphanin FQ is a Functional Anti-Opioid Peptide", Neuroscience, 1996, pp. 333-337, vol. 75, No. 2, Elsevier Science Ltd., Great Britain.

Miyuki Nishi et al., "Unrestrained Nociceptive Response and Dlsregulation of Hearing Ability in Mice Lacking the Nociceptin/OrphaninFQ Receptor," The EMBO Journal, 1997, pp. 1858-1864, vol. 16, No. 8, Oxford University Press.

Rainer K. Reinscheid et al., "Orphanin FQ: A Neuropeptide That Activates an Opioldlike G Protein-Coupled Receptor," Science, Nov. 3, 1995, pp. 792-794, vol. 270.

Christopher W. Vaughan et al., "Increase by the $ORL_1$ Receptor (Opioid Receptor-$like_1$) Ligand, Nociceptin, of Inwardly Rectifying K Conductance in Dorsal Raphe Nucleus Neurones," Special Report, pp. 1609-1611, 1996.

Tatsuo Yamamoto et al., "Effects of Intrathecally Administered Nociceptin, an Opioid Receptor-$like_1$ Receptor Agonist, and N-methyl-D-aspartate Receptor Antagonist on the Thermal Hyperalgesia Induced by Partial Sciatic Nerve Injury in the Rat," Anesthesiology, 1997, pp. 1145-1152, vol. 87, No. 5, Lippincott-Raven Publishers.

Ali Ardati et al., "Interaction of [$^3$H]Orphanin FQ and $^{125}$I-Tyr14-Orphanin FQ with the Orphanin FQ Receptor: Kinetics and Modulation by Cations and Guanine Nucleotides," Molecular Pharmacology, 1997, pp. 816-824, 51, The American Society for Pharmacology and Experimental Therapeutics.

Hunter C. Champion et al., "[$Tyr^1$]-Nociceptin, a Novel Nociceptin Analog, Decreases Systemic Arterial Pressure by a Naloxone-Insensitive Mechanism in the Rat," Biochemical and Biophysical Research Communications, 1997, pp. 309-312, 234, Academic Press.

Tristan Darland et al., "Orphanin FQ/nociceptin: a Role in Pain and Analgesia, But So Much More," TINS, 1998, pp. 215-221, vol. 21, No. 5, Elsevier Science Ltd.

Bulent Gumusel et al., "Nociceptin: An Endogenous Agonist for Central Opioid $Like_1$ ($ORL_1$) Receptors Possesses Systemic Vasorelaxant Properties," Life Sciences, 1997, pp. PL 141-145, vol. 60, No. 8, Elsevier Science Inc., USA.

Naoki Hara et al., "Characterization of Nociceptin Hyperalgesia and Allodynia in Conscious Mice," British Journal of Pharmacology, 1997, pp. 401-408, 121, Stockton Press.

Daniel R. Kapusta et al., "Diuretic and Antinatriuretic Responses Produced by the Endogenous Opioid-Like Peptide, Nociceptin (Orphanin FQ)," Life Sciences, 1997, pp. PL 15-21, vol. 60, No. 1, Elsevier Science Inc., USA.

Frederic Knoflach et al., "Modulation of Voltage-Gated Calcium Channels by Orphanin FQ in Freshly Dissociated Hippocampal Neurons," The Journal of Neuroscience, Nov. 1, 1996, pp. 6657-6664, 16, 21, Society for Neuroscience.

Hans Matthes et al., "Functional Selectivity of Orphanin FQ for Its Receptor Coexpressed with Potassium Channel Subunits in Xenopus laevis Oocytes," Molecular Pharmacology, 1996, pp. 447-450, 50, The American Society for Pharmacology and Experimental Therapeutics.

Jeffrey S. Mogil et al., "Functional Antagonism of $\mu$-, $\sigma$- and $\kappa$-opioid Antinociception by Orphanin FQ," Neuroscience Letters, 1996, pp. 131-134, 214, Elsevier Science Ireland Ltd.

Catherine Mollereau et al., "ORL1, A Novel Members of the Opioids Receptor Family Cloning, Functional Expression and Localization," FEBS Letters, 1994, 341, Federation of European Biochemical Societies.

James D. Pomonis et al., "Orphanin FQ, Agonist of Orphan Opioid Receptor $ORL_1$, Stimulates Feeding in Rats," NeuroReport, Dec. 20, 1996, pp. 369-371, vol. 8, No. 1, Rapid Science Publishers.

Y.-S. Shu et al., "Orphanin FQ/Nociceptin Modulates Glutamate- and Kainic Acid-Induced Currents in Acutely Isolated Rat Spinal Dorsal Horn Neurons," Neuropeptides, 1998, pp. 567-571, 32, Harcourt Brace & Co., Ltd.

Xiao-Jun Xu et al., "Nociceptin or Antinociceptin: Potent Spinal Antinociceptive Effect of Orphanin FQ/ Nociceptin in the Rat," NeuroReport, Sep. 2, 1996, vol. 17, No. 13, Rapid Science Publishers.

T. Yamamoto et al., "Analgesic Effect of Intrathecally Administered Nociceptin, an Opioid Receptor-$Like_1$ Receptor Agonist, in the Rat Formalin Test," Neuroscience, 1997, pp. 249-254, vol. 81, Elsevier Science Ltd.

* cited by examiner

SUBSTITUTED 4-AMINOCYCLOHEXANOL COMPOUNDS

CROSS-REFERENCE TO RELATED APPLICATION

This application is a continuation of International Patent Application No. PCT/EP02/07849, filed Jul. 15, 2002, designating the United States of America, and published in German as WO 03/008371, the entire disclosure of which is incorporated herein by reference. Priority is claimed based on Federal Republic of Germany Patent Application Nos. DE 101 35 637.4, filed Jul. 17, 2001 and DE 101 35 635.8, filed Jul. 17, 2001.

FIELD OF THE INVENTION

The present invention relates to substituted 4-aminocyclohexanol derivatives, processes for their preparation, pharmaceutical formulations comprising these compounds and the use of substituted 4-aminocyclohexanol derivatives for the preparation of pharmaceutical formulations for treatment of diverse indications, including, without limitation, pain and for the treatment or inhibition of diverse indications, including, without limitation, pain.

BACKGROUND OF THE INVENTION

The heptadecapeptide nociceptin is an endogenous ligand of the ORL1 (opioid receptor-like) receptor (Meunier et al., Nature 377, 1995, p. 532-535), which belongs to the family of opioid receptors and is to be found in many regions of the brain and spinal cord (Mollereau et al., FEBS Letters, 341, 1994, p. 33-38, Darland et al., Trends in Neurosciences, 21, 1998, p. 215-221). The peptide is characterized by a high affinity, with a $K_d$ value of approximately 56 pM (Ardati et al., Mol. Pharmacol. 51, p. 816-824), and by a high selectivity for the ORL1 receptor. The ORL1 receptor is homologous to the μ, κ and δ opioid receptors and the amino acid sequence of the nociceptin peptide has a high similarity with those of the known opioid peptides. The activation of the receptor induced by nociceptin leads, via coupling with $G_{i/o}$ proteins, to an inhibition of adenylate cyclase (Meunier et al., Nature 377, 1995, p. 532-535). Functional similarities of the μ, κ and δ opioid receptors with the ORL1 receptor are also present at the cell level in respect of activation of the potassium channel (Matthes et al., Mol. Pharmacol. 50, 1996, p. 447-450; Vaughan et al., Br. J. Pharmacol. 117, 1996, p. 1609-1611) and inhibition of the L-, N- and P/Q-type calcium channels (Conner et al., Br. J. Pharmacol. 118, 1996, p. 205-207; Knoflach et al., J. Neuroscience 16, 1996, p. 6657-6664).

The nociceptin peptide shows a pronociceptive and hyperalgesic activity after intercerebroventicular administration in various animal models (Reinscheid et al., Science 270, 1995, p. 792-794; Hara et al,. Br. J. Pharmacol. 121, 1997, p. 401-408). These findings can be explained as inhibition of stress-induced analgesia (Mogil et al., Neurosci. Letters 214, 1996, p 131-134; and Neuroscience 75, 1996, p. 333-337). In this connection it has also been possible to demonstrate an anxiolytic activity of nociceptin (Jenck et al., Proc. Natl. Acad. Sci. USA 94, 1997, 14854-14858).

On the other hand, it has also been possible to show an antinociceptive effect of nociceptin in various animal models, in particular after intrathecal administration. Nociceptin inhibits the activity of kainate- or glutamate-stimulated dorsal root ganglia neurons (Shu et al., Neuropeptides, 32, 1998, 567-571) or glutamate-stimulated spinal cord neurons (Faber et al., Br. J. Pharmacol., 119, 1996, p. 189-190); it has an antinociceptive action in the tail flick test in the mouse (King at al., Neurosci. Lett., 223, 1997, 113-116), in the flexor-reflex model in the rat (Xu et al., NeuroReport, 7, 1996, 2092-2094) and in the formalin test on the rat (Yamamoto et al., Neuroscience, 81, 1997, p. 249-254). In models for neuropathic pain it has also been possible to demonstrate an antinociceptive action of nociceptin (Yamamoto and Nozaki-Taguchi, Anesthesiology, 87, 1997), which is of interest in as much as the activity of nociceptin increases after axotomy of spinal nerves. This is in contrast to conventional opioids, the activity of which decreases under these conditions (Abdulla and Smith, J. Neurosci., 18, 1998, p. 9685-9694).

The ORL1 receptor is moreover also involved in the regulation of further physiological and pathophysiological processes. These include, inter alia, learning and memory formation (Sandin et al., Eur. J. Neurosci., 9, 1997, p. 194-197; Manabe et al., Nature, 394, 1997, p. 577-581), hearing ability (Nishi et al., EMBO J., 16, 1997, p. 1858-1864), food intake (Pomonis et al., NeuroReport, 8, 1996, p. 369-371), regulation of blood pressure (Gumusel et al., Life Sci., 60, 1997, p. 141-145; Campion and Kadowitz, Biochem. Biophys. Res. Comm., 234, 1977, p. 309-312), epilepsy (Gutiérrez et al, Abstract 536.18, Society for Neuroscience, vol. 24, 28th Ann. Meeting, Los Angeles, Nov. 7th-12th, 1998) and diuresis (Kapista et al., Life Sciences, 60, 1997, PL 15-21). In a review article by Calo et al. (Br. J. Pharmacol., 129, 2000, 1261-1283) an overview of the indications or biological processes in which the ORL1 receptor plays or with high probability could play a role is given. There are mentioned, inter alia: analgesia, stimulation and regulation of food intake, influence on μ-agonists, such as morphine, treatment of withdrawal symptoms, reduction in the addiction potential of morphines, anxiolysis, modulation of motor activity, memory disorders, epilepsy; modulation of neurotransmitter secretion, in particular of glutamate, serotonin and dopamine, and therefore neurodegenerative diseases; influencing of the cardiovascular system, initiation of an erection, diuresis, antinatriuresis, electrolyte balance, arterial blood pressure, water retention diseases, intestinal motility (diarrhea), relaxing effects on the respiratory tract, micturation reflex (urinary incontinence). The use of agonists and antagonists as anoretics, analgesics (also in co-administration with opioids) or nootropics, and also as antitussives is furthermore discussed.

The possible uses of compounds which bond to the ORL1 receptor and activate or inhibit this are correspondingly diverse.

SUMMARY OF THE INVENTION

One object of the present invention was to provide active compounds which act on the nociceptin/ORL1 receptor system and are therefore suitable for pharmaceutical formulations, in particular for treatment of the various diseases which, according to the prior art, are connected with this system, or for use in the indications mentioned there.

The invention therefore provides substituted 4-aminocyclohexanol compounds corresponding to formula I

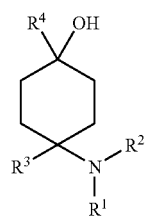

I wherein
$R^1$ and $R^2$ independently of one another are chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl bonded via $C_{1-3}$-alkylene and in each case mono- or polysubstituted or unsubstituted; wherein $R^1$ and $R^2$ may not both be H, or the radicals $R^1$ and $R^2$ together form a ring and denote $CH_2CH_2OCH_2CH_2$, $CH_2CH_2NR^5CH_2CH_2$ or $(CH_2)_{3-6}$,
  where $R^5$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl bonded via $C_{1-3}$-alkylene and in each case mono- or polysubstituted or unsubstituted;
$R^3$ is chosen from $C_{1-8}$-alkyl or $C_{3-8}$-cycloalkyl, in each case saturated or unsaturated, branched or unbranched, mono- or polysubstituted or unsubstituted; or aryl, $C_{3-8}$-cycloalkyl or heteroaryl bonded via a saturated or unsaturated, branched or unbranched, substituted or unsubstituted $C_{1-4}$-alkyl group and in each case unsubstituted or mono- or polysubstituted;
$R^4$ is chosen from $C_{3-8}$-cycloalkyl, aryl or heteroaryl, in each case unsubstituted or mono- or polysubstituted; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$—$L$—$R^9$
  where Y=O, S or $H_2$,
  where $R^6$ is chosen from
    H, $C_{1-7}$-alkyl, saturated or unsaturated, branched or unbranched, mono- or polysubstituted or unsubstituted; or C(O)O—$C_{1-6}$-alkyl, saturated or unsaturated, branched or unbranched, mono- or polysubstituted or unsubstituted;
  and where R7 is chosen from
    H; $C_{3-8}$-cycloalkyl, aryl or heteroaryl, in each case unsubstituted or mono- or polysubstituted,
  where $R^8$ is chosen from
    aryl or heteroaryl, in each case unsubstituted or mono- or polysubstituted,
  where L is chosen from
    —C(O)—NH—, —NH—C(O)—, —C(O)—O—, —O—C(O)—, —O—, —S— or —S(O)$_2$—
  where $R^9$ is chosen from
    aryl or heteroaryl, in each case unsubstituted or mono- or polysubstituted,
optionally in the form of their racemates, their pure stereoisomers, in particular enantiomers or diastereomers, or in the form of mixtures of the stereoisomers, in particular the enantiomers or diastereomers, in any desired mixing ratio;
in the form shown or in the form of their acids or their bases or in the form of their salts, in particular the physiologically acceptable salts, or in the form of their solvates, in particular the hydrates.

All these compounds or compound groups according to the invention show outstanding binding to the ORL1 receptor.

Compounds which show a certain remote structural relationship to the compounds proposed here are known from the following publications:
  DE-OS-28 39 891 or the parallel U.S. patent U.S. Pat. No. 4,366,172 (Lednicer et al.). In this the compounds mentioned are described as analgesically active, without reference being made to the ORL1 receptor.

The parallel articles:
  D. Lednicer and P. F. von Voightlander, J. Med. Chem. 1979, 22, 1157,
  D. Lednicer, P. F. von Voightlander and D. E. Emmert, J. Med. Chem. 1980, 23, 424, and
  D. Lednicer, P. F. von Voightlander and D. E. Emmert, J. Med. Chem. 1981, 24, 404,
  D. Lednicer, P. F. von Voightlander and D. E. Emmert, J. Med. Chem. 1981, 24, 340,
  P. F. VonVoightlander, D. Lednicer, R. A. Lewis and D. D. Gay, "Endogenous and Exogenous Opiate Agonists and Antagonists", Proc. Int. Narc. Res. Club Conf. (1980), Meeting Date 1979, Way E. Long (Ed), Publisher: Pergamon, Elmsford, N.Y. International, Pergamon, 1980, 17-21,
  Kamenka et al., Eur J. Med. Chem. Chim.Ther.; FR; 19;3; 1984;255-260 and
  Rao M. N. A. and Rao S. C. Indian Drugs, 1985, 22 (5), 252-257.

In the context of this invention, alkyl or cycloalkyl radicals are understood as meaning saturated and unsaturated (but not aromatic), branched, unbranched and cyclic hydrocarbons, which can be unsubstituted or mono- or polysubstituted. Here, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4- or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. Furthermore, $C_{3-4}$-cycloalkyl represents C3- or C4-cycloalkyl, C3-5-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. In respect of cycloalkyl, the term also includes saturated cycloalkyls in which one or 2 carbon atoms are replaced by a heteroatom, S, N or O. The term cycloalkyl, however, also includes, in particular, mono- or poly-, preferably monounsaturated cycloalkyls without a heteroatom in the ring, as long as the cycloalkyl does not represent an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also adamantyl, $CHF_2$, $CF_3$ or $CH_2OH$ as well as pyrazolinone, oxopyrazolinone, [1,4]dioxane or dioxolane.

In connection with alkyl and cycloalkyl—as long as this is not expressly defined otherwise—the term substituted is understood here in the context of this invention as meaning substitution of at least one (optionally also several) hydrogen radical(s) by F, Cl, Br, I, $NH_2$, SH or OH, where "polysubstituted" or "substituted" in the case of polysubstitution is to be understood as meaning that the substitution can be both on different and on the same atoms several times with the same or different substituents, for example three times on the same C atom, as in the case of $CF_3$, or at different places, as in the case of —CH(OH)—CH=CH—$CHCl_2$. Particularly preferred substituents here are F, Cl and OH. In respect of cycloalkyl, the hydrogen radical can also be replaced by $OC_{1-3}$-alkyl or $C_{1-3}$-alkyl (in each case mono- or polysubstituted or unsubstituted), in particular methyl, ethyl, n-propyl, i-propyl, $CF_3$, methoxy or ethoxy.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is to be understood as meaning —$CH_2$—$CH_2$—$CH_2$—$CH_2$— and —$CH_2$—$CH_2$—$CH_2$—$CH_2$—$CH_2$—, etc.

An aryl radical is understood as meaning ring systems with at least one aromatic ring but without heteroatoms in even only one of the rings. Examples are phenyl, naphthyl, fluoranthenyl, fluorenyl, tetralinyl or indanyl, in particular 9H-fluorenyl or anthracenyl radicals, which can be unsubstituted or mono- or polysubstituted.

A heteroaryl radical is understood as meaning heterocyclic ring systems which have at least one unsaturated ring and contain one or more heteroatoms from the group consisting of nitrogen, oxygen and/or sulfur and can also be mono- or polysubstituted. Examples which may be mentioned from the group of heteroaryls are furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolane, benzodioxane, carbazole, indole and quinazoline.

In connection with aryl and heteroaryl, substituted here is understood as meaning substitution of the aryl or heteroaryl with $R^{82}$, $OR^{82}$ a halogen, preferably F and/or Cl, a $CF_3$, a CN, an $NO_2$, an $NR^{83}R^{84}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

The radical $R^{82}$ here represents H, a $C_{1-10}$-alkyl, preferably a $C_{1-6}$-alkyl, an aryl or heteroaryl, or an aryl or heteroaryl radical bonded via $C_{1-3}$-alkyl, saturated or unsaturated, or a $C_{1-3}$-alkylene group, where these aryl and heteroaryl radicals may not themselves be substituted by aryl or heteroaryl radicals, the radicals $R^{83}$ and $R^{84}$, which are identical or different, denote for H, a $C_{1-10}$-alkyl, preferably a $C_{1-6}$-alkyl, an aryl, a heteroaryl, or an aryl or heteroaryl radical bonded via $C_{1-3}$-alkyl, saturated or unsaturated, or a $C_{1-3}$-alkylene group, where these aryl and heteroaryl radicals may not themselves be substituted by aryl or heteroaryl radicals, or the radicals $R^{83}$ and $R^{84}$ together denote $CH_2CH_2OCH_2CH_2$, $CH_2CH_2NR^{85}CH_2CH_2$ or $(CH_2)_{3-6}$, and the radical $R^{85}$ for H, a $C_{1-10}$-alkyl, preferably a $C_{1-6}$-alkyl, an aryl or heteroaryl radical, or an aryl or heteroaryl radical bonded via $C_{1-3}$-alkyl, saturated or unsaturated, or a $C_{1-3}$-alkylene group, where these aryl and heteroaryl radicals may not themselves be substituted by aryl or heteroaryl radicals.

The term salt is to be understood as meaning any form of the active compound according to the invention in which this assumes an ionic form or is charged and is coupled with a counter-ion (a cation or anion) or is in solution. This is also to be understood as meaning complexes of the active compound with other molecules and ions, in particular complexes which are complexed via ionic interactions. In particular this is understood as meaning (and this is also a preferred embodiment of this invention) physiologically acceptable salts, in particular physiologically acceptable salts with cations or bases and physiologically acceptable salts with anions or acids or also a salt formed with a physiologically acceptable acid or a physiologically acceptable cation.

Physiologically acceptable is to be understood as meaning that the substance, in particular the salt as such, is acceptable when used on humans or mammals, that is to say, for example, does not have a non-physiological (e.g. toxic) action.

The term of the physiologically acceptable salt with anions or acids is understood in the context of this invention as meaning salts of at least one of the compounds according to the invention—usually protonated, for example on the nitrogen—as the cation with at least one anion, which are physiologically acceptable—in particular when used on humans and/or mammals. In particular, in the context of this invention this is understood as meaning the salt formed with a physiologically acceptable acid, namely salts of the particular active compound with inorganic or organic acids which are physiologically acceptable—in particular when used on humans and/or mammals. Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydrol $\lambda^6$-enzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, acetylsalicylic acid, hippuric acid and/or aspartic acid. The hydrochloride salt is particularly preferred.

The term of the salt formed with a physiologically acceptable acid is understood in the context of this invention as meaning salts of the particular active compound with inorganic or organic acids which are physiologically acceptable—in particular when used on humans and/or mammals. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydrol$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, acetylsalicylic acid, hippuric acid and/or aspartic acid.

The term of the physiologically acceptable salt with cations or bases is understood in the context of this invention as meaning salts of at least one of the compounds according to the invention—usually of a (deprotonated) acid—as the anion with at least one, preferably inorganic cation, which are physiologically acceptable—in particular when used on humans and/or mammals. Salts which are particularly preferred are those of the alkali metals and alkaline earth metals, but also with $NH_4^+$, but in particular (mono-) or (di-)sodium, (mono-) or (di-)potassium, magnesium or calcium salts.

The term of the salt formed with a physiologically acceptable cation is understood in the context of this invention as meaning salts of at least one of the particular compounds as the anion with at least one inorganic cation, which is physiologically acceptable—in particular when used on humans and/or mammals. Salts which are particularly preferred are those of the alkali metals and alkaline earth metals, but also $NH_4^+$, but in particular (mono-) or (di-)sodium, (mono-) or (di-)potassium, magnesium or calcium salts.

In respect of the substituted 4-aminocyclohexanol derivatives according to the invention described above, it is preferable if $R^1$ and $R^2$ independently of one another are chosen from H; $C_{1-8}$-alkyl, saturated or unsaturated, branched or unbranched, mono- or polysubstituted or unsubstituted; where $R^1$ and $R^2$ may not both be H, or the radicals $R^1$ and $R^2$ together form a ring and denote $CH_2CH_2OCH_2CH_2$, $CH_2CH_2NR^5CH_2CH_2$ or $(CH_2)_{3-6}$, where $R^5$ is chosen from H; $C_{1-8}$-alkyl, saturated or unsaturated, branched or unbranched, mono- or polysubstituted or unsubstituted, preferably $R^1$ and $R^2$ independently of one another are chosen from H; $C_{1-4}$-alkyl, saturated or unsaturated, branched or unbranched, mono- or polysubstituted or unsubstituted; where $R^1$ and $R^2$ may not both be H, or the radicals $R^1$ and $R^2$ together form a ring and denote $(CH_2)_{4-5}$, in particular $R^1$ and $R^2$ independently of one another are chosen from methyl or ethyl or the radicals $R^1$ and $R^2$ together form a ring and denote $(CH_2)_5$.

In respect of the substituted 4-aminocyclohexanol derivatives according to the invention described above, it is preferable if $R^3$ is chosen from $C_{3-8}$-cycloalkyl, unsubstituted or mono- or polysubstituted; or aryl, $C_{3-8}$-cycloalkyl or heteroaryl bonded via a saturated or unsaturated, unbranched, substituted or unsubstituted $C_{1-4}$-alkyl group and in each case unsubstituted or mono- or polysubstituted;

preferably $R^3$ is chosen from $C_{5-6}$-cycloalkyl, unsubstituted or mono- or polysubstituted; or $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched $C_{1-2}$-alkyl group and in each case unsubstituted or mono- or polysubstituted;

in particular $R^3$ is chosen from phenyl, pyridyl, furyl or thiophenyl bonded via a saturated, unbranched $C_{1-2}$-alkyl group and in each case unsubstituted or mono- or polysubstituted.

In respect of the substituted 4-aminocyclohexanol derivatives according to the invention described above, it is preferable if $R^4$ is chosen from $C_{3-8}$-cycloalkyl, aryl or heteroaryl, in each case unsubstituted or mono- or polysubstituted; or $-R^8-L-R^9$ preferably $R^4$ is chosen from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted; or $-R^8-L-R^9$ in particular $R^4$ is chosen from cyclopentyl, cyclohexyl, cycloheptyl, cyclooctyl, anthracenyl, indolyl, naphthyl, benzothiazolyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted; or $-R^8-L-R^9$.

In respect of the preferred embodiment directly above, in respect of $R^4$ it is furthermore preferable if $R^8$ is chosen from indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl, in each case unsubstituted or mono- or polysubstituted, L is chosen from —C(O)—NH—, —NH—C(O)—, —C(O)—O—, —O—C(O)—, —O—, —S— or —S(O)$_2$—, and/or $R^9$ is chosen from indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl, in each case unsubstituted or mono- or polysubstituted, preferably $R^8$ is chosen from indolyl, benzothiophenyl, phenyl, thiophenyl, furyl, pyridyl, pyrrolyl, pyrazinyl or pyrimidyl, in each case unsubstituted or mono- or polysubstituted, L is chosen from —C(O)—NH—, —NH—C(O)—, —C(O)—O—, —O—C(O)— or —S(O)$_2$—, and/or $R^9$ is chosen from indolyl, benzothiophenyl, phenyl, thiophenyl, furyl, pyridyl, pyrrolyl, pyrazinyl or pyrimidyl, in each case unsubstituted or mono- or polysubstituted, in particular $R^8$ is chosen from indolyl, unsubstituted, L is chosen from

—S(O)$_2$— and $R^9$ is chosen from phenyl, unsubstituted.

In a further embodiment, it is preferable if, in respect of the substituted 4-aminocyclohexanol derivatives according to the invention described, $R^4$ is chosen from —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$ where Y=O, S or H$_2$, preferably $R^4$ is chosen from —CHR$^6$R$^7$, —CHR$^6$—CH$_2$R$^7$, —CHR$^6$—CH$_2$—CH$_2$R$^7$, —C(Y)R$^7$,—C(Y)—CH$_2$R$^7$ or —C(Y)—CH$_2$—CH$_2$R$^7$ where Y=O or S, in particular $R^4$ is chosen from —CHR$^6$R$^7$, —CHR$^6$—CH$_2$R$^7$, —C(Y)R$^7$ or —C(Y)—CH$_2$R$^7$ where Y=O.

In respect of the preferred embodiment directly above, in respect of $R^4$ it is furthermore preferable if $R^6$ is chosen from H, $C_{1-4}$-alkyl, saturated or unsaturated, branched or unbranched, mono- or polysubstituted or unsubstituted; or C(O)O-$C_{1-4}$-alkyl, saturated or unsaturated, branched or unbranched, mono- or polysubstituted or unsubstituted; preferably H, $C_{1-4}$-alkyl, saturated or unsaturated, branched or unbranched, mono- or polysubstituted or unsubstituted;

in particular

H, $CH_3$ and $C_2H_5$.

In respect of the preferred embodiment directly above, in respect of $R^4$ it is furthermore also preferable if $R^7$ is chosen from $C_{3-8}$-cycloalkyl, aryl or heteroaryl, in each case unsubstituted or mono- or polysubstituted; preferably $R^7$ is chosen from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted;

in particular $R^7$ is chosen from cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted.

In respect of the substituted 4-aminocyclohexanol derivatives according to the invention described, it is preferable if they are chosen from the following group:

4-benzyl-4-dimethylamino-1-phenethylcyclohexanol and the corresponding hydrochloride, 4-dimethylamino-1,4-diphenethylcyclohexanol and the corresponding hydrochloride, 4-benzyl-4-dimethylamino-1-[2-(2-fluorophenyl)ethyl]cyclohexanol and the corresponding hydrochloride, 4-benzyl-4-dimethylamino-1-[2-(4-fluorophenyl)ethyl]cyclohexanol and the corresponding hydrochloride, 4-dimethylamino-4-(2-fluorobenzyl)-1-phenethylcyclohexanol and the corresponding hydrochloride, 4-dimethylamino-4-(3-fluorobenzyl)-1-phenethylcyclohexanol and the corresponding hydrochloride, 4-dimethylamino-4-(4-fluorobenzyl)-1-phenethylcyclohexanol and the corresponding hydrochloride, 4-benzyl-4-dimethylamino-1-[2-(3-fluorophenyl)ethyl]cyclohexanol and the corresponding hydrochloride 4-benzyl-4-dimethylamino-1-(2-fluorobenzyl)cyclohexanol and the corresponding hydrochloride, 4-(allylmethylamino)-4-benzyl-1-phenethylcyclohexanol and the corresponding hydrochloride, 4-benzyl-4-dimethylamino-1-(3-fluorobenzyl)cyclohexanol and the corresponding hydrochloride, 4-benzyl-4-dimethylamino-1-(4-fluorobenzyl)cyclohexanol and the corresponding hydrochloride, 1-benzyl-4-dimethylamino-4-(3-fluorobenzyl)cyclohexanol and the corresponding hydrochloride or 4-benzyl-1-phenethyl-4-pyrrolidin-1-ylcyclohexanol and the corresponding hydrochloride 4-benzyl-4-dimethylamino-1-(1-methyl-1H-indol-2-yl)cyclohexanol 1-benzo[b]thiophen-2-yl-4-benzyl-4-dimethylaminocyclohexanol 1-benzo[b]thiophen-3-yl-4-benzyl-4-dimethylaminocyclohexanol 1-benzofuran-2-yl-4-benzyl-4-dimethylamino-cyclohexanol optionally in the form of their racemates, their pure stereoisomers, in particular enantiomers or diastereomers, or in the form of mixtures of the stereoisomers, in particular the enantiomers or diastereomers, in any desired mixing ratio;

in the form shown or in the form of their acids or their bases or in the form of their salts, in particular the physiologically acceptable salts, or in the form of their solvates, in particular the hydrates.

The substances according to the invention are toxicologically acceptable, so that they are suitable as a pharmaceutical active compound in medicaments.

The invention therefore also provides pharmaceutical formulations comprising at least one substituted 4-aminocyclohexanol derivative according to the invention, optionally in the form of its racemate, the pure stereoisomers, in particular enantiomers or diastereomers, or in the form of mixtures of the stereoisomers, in particular the enantiomers or diastereomers, in any desired mixing ratio; in the form shown or in the form of the acids or the bases or in the form of the salts, in particular the physiologically acceptable salts, or in the form of the solvates, in particular the hydrates; and optionally suitable additives and/or auxiliary substances and/or optionally further active compounds.

In addition to at least one substituted 4-aminocyclohexanol derivative according to the invention, the pharmaceutical formulations according to the invention optionally comprise suitable additives and/or auxiliary substances, thus also carrier materials, fillers, solvents, diluents, dyestuffs and/or binders, and can be administered as liquid medicament forms in the form of injection solutions, drops or juices, as semi-solid medicament forms in the form of granules, tablets, pellets, patches, capsules, patches or aerosols. The choice of the auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example on the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Substituted 4-aminocyclohexanol derivatives according to the invention in a depot, in dissolved form or in a patch, optionally with the addition of agents which promote penetration through the skin, are suitable formulations for percutaneous administration. Formulation forms for oral or percutaneous use can release the substituted 4-aminocyclohexanol derivatives according to the invention in a delayed manner. In principle, other further active compounds known to the expert can be added to the medicaments according to the invention.

The amount of active compound to be administered to the patients varies as a function of the weight of the patient, the mode of administration, the indication and the severity of the disease. 0.005 to 1,000 mg/kg, preferably 0.05 to 5 mg/kg of at least one substituted 4-aminocyclohexanol derivative according to the invention are conventionally administered.

For all the above forms of the medicaments according to the invention, it is particular preferable if the medicament also comprises, in addition to at least one substituted 4-aminocyclohexanol derivative, an opioid, preferably a potent opioid, in particular morphine, or an anesthetic, preferably hexobarbital or halothane.

In a preferred form of the medicament, a substituted 4-aminocyclohexanol derivative according to the invention contained therein is present as the pure diastereomer and/or enantiomer, as a racemate or as a non-equimolar or equimolar mixture of the diastereomers and/or enantiomers.

As can be seen from the prior art in the introduction, the ORL1 receptor has been identified in particular in the pain event. Substituted 4-aminocyclohexanol derivatives according to the invention can accordingly be used for the preparation of a medicament for treatment of pain, in particular acute, visceral, neuropathic or chronic pain.

The invention therefore also provides the use of a substituted 4-aminocyclohexanol derivative according to the invention, optionally in the form of its racemates, its pure stereoisomers, in particular enantiomers or diastereomers, or in the form of mixtures of the stereoisomers, in particular the enantiomers or diastereomers, in any desired mixing ratio; in the form shown or in the form of its acids or its bases or in the form of its salts, in particular the physiologically acceptable salts, or in the form of its solvates, in particular the hydrates, for the preparation of a pharmaceutical formulation for treatment of pain, in particular acute, visceral, neuropathic or chronic pain.

As already stated in the introduction, in addition to the function in the pain event, the ORL1 receptor also plays a role in a large number of other physiological processes, in particular of medically relevant importance.

The invention therefore also provides the use of a substituted 4-aminocyclohexanol derivative according to the invention, optionally in the form of its racemates, its pure stereoisomers, in particular enantiomers or diastereomers, or in the form of mixtures of the stereoisomers, in particular the enantiomers or diastereomers, in any desired mixing ratio; in the form shown or in the form of its acids or its bases or in the form of its salts, in particular the physiologically acceptable salts, or in the form of its solvates, in particular the hydrates, for the preparation of a pharmaceutical formulation for treatment of anxiety states, of stress and stress-associated syndromes, depressions, epilepsy, Alzheimer's disease, senile dementia, general cognitive dysfunctions, learning and memory difficulties (as a nootropic), withdrawal symptoms, alcohol and/or drug and/or pharmaceutical formulation abuse and/or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhea, cachexia, urinary incontinence or as a muscle relaxant, anticonvulsive, antitussive or anesthetic or for co-administration in treatment with an opioid analgesic or with an anesthetic, for diuresis or antinatriuresis and/or anxiolysis.

In one of the above uses it may be preferable here if a substituted 4-aminocyclohexanol derivative used is present as the pure diastereomer and/or enantiomer, as a racemate or as a non-equimolar or equimolar mixture of the diastereomers and/or enantiomers, and/or, in addition to the substituted 4-aminocyclohexanol derivative, for an opioid, preferably a potent opioid, in particular morphine, or an anesthetic, preferably hexobarbital or halothane, to be used.

The invention also provides a method for treatment, in particular in one of the abovementioned indications, of a non-human mammal or human which or who requires treatment of pain, in particular chronic pain, by administration of a therapeutically active dose of a substituted cyclohexane-1, 4-diamine derivative according to the invention or of a pharmaceutical formulation according to the invention.

The invention also provides a process for the preparation of the substituted 4-aminocyclohexanol derivatives according to the invention as described in the following description and examples.

A process with the following steps is particularly suitable here:

a. a cyclohexane-1,4-dione, protected with the groups $S^1$ and $S^2$, according to formula II is reacted with a cyanide, preferably potassium cyanide, in the presence of a compound of the formula $HNR^{01}R^{02}$ to give a protected N-substituted 1-amino-4-oxo-cyclohexanecarbonitrile derivative according to formula III;

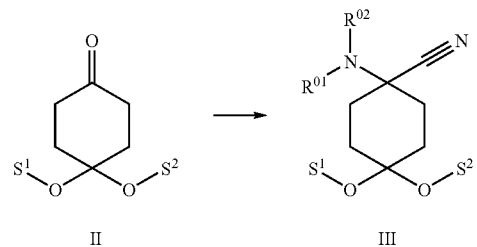

optionally acylation, alkylation or sulfonation is then carried out in any desired sequence and optionally repeatedly, and/or in the case of compounds where $R^{01}$ and/or $R^{02}$ and/or $R^{06}$=H protected with a protective group, at least once a protective group is removed and optionally acylation, alkylation or sulfonation is carried out, and/or in the case of a compounds where $R^{01}$ and/or $R^{02}$ and/or $R^{06}$=H, at least once a protective group is introduced and optionally acylation, alkylation or sulfonation is carried out, b. the aminonitrile according to formula III is reacted with organometallic reagents, preferably Grignard or organolithium reagents, of the formula metal-$R^3$, so that a compound according to formula IVa is formed;

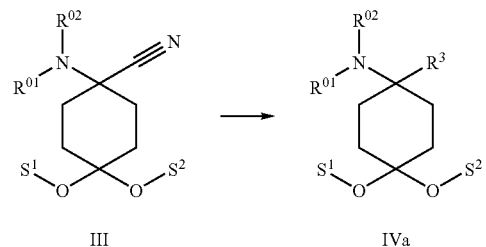

optionally acylation, alkylation or sulfonation is then carried out in any desired sequence and optionally repeatedly, and/or in the case of compounds where $R^{01}$ and/or $R^{02}$ and/or $R^{06}$=H protected with a protective group, at least once a protective group is removed and optionally acylation, alkylation or sulfonation is carried out, and/or in the case of a compounds where $R^{01}$ and/or $R^{02}$ and/or $R^{06}$=H, at least once a protective group is introduced and optionally acylation, alkylation or sulfonation is carried out, c. on the compound according to formula IVa according to formula III, the protective groups $S^1$ and $S^2$ are removed so that a 4-substituted 4-aminocyclohexanone derivative according to formula IV is formed;

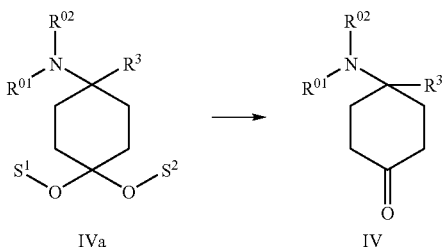

optionally acylation, alkylation or sulfonation is then carried out in any desired sequence and optionally repeatedly, and/or in the case of compounds where $R^{01}$ and/or $R^{02}$ and/or $R^{06}$=H protected with a protective group, at least once a protective group is removed and optionally acylation, alkylation or sulfonation is carried out, and/or in the case of a compounds where $R^{01}$ and/or $R^{02}$ and/or $R^{06}$=H, at least once a protective group is introduced and optionally acylation, alkylation or sulfonation is carried out, d. the 4-substituted 4-aminocyclohexanone derivative according to formula IV is reacted with organometallic reagents, preferably Grignard or organolithium reagents, of the formula metal-$R^3$ so that a compound according to formula V is formed;

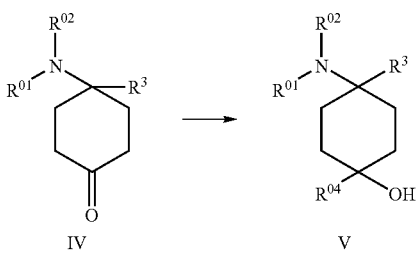

optionally acylation, alkylation or sulfonation is then carried out in any desired sequence and optionally repeatedly, and/or in the case of compounds where $R^{01}$ and/or $R^{02}$ and/or $R^{04}$ and/or $R^{05}$ and/or $R^{06}$=H protected with a protective group, at least once a protective group is removed and optionally acylation, alkylation or sulfonation is carried out, and/or in the case of a compounds where $R^{01}$ and/or $R^{02}$ and/or $R^{04}$ and/or $R^{05}$ and/or $R^{06}$=H, at least once a protective group is introduced and optionally acylation, alkylation or sulfonation is carried out, until a compound according to formula I is formed, wherein $R^1$, $R^2$, $R^3$, $R^4$ and $R^5$ have the meaning given in claim 1 and $R^{01}$ and $R^{02}$ independently of one another are chosen from H; H provided with a protective group; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl bonded via $C_{1-3}$-alkylene and in each case mono- or polysubstituted or unsubstituted;

or the radicals $R^{01}$ and $R^{02}$ together form a ring and denote $CH_2CH_2OCH_2CH_2$, $CH_2CH_2NR^{05}CH_2CH_2$ or $(CH_2)_{3-6}$, where $R^{05}$ is chosen from H; H provided with a protective group; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl bonded via $C_{1-3}$-alkylene and in each case mono- or polysubstituted or unsubstituted;

$R^{04}$ is chosen from H, H provided with a protective group; $C_{3-8}$-cycloalkyl, aryl or heteroaryl, in each case unsubstituted or mono- or polysubstituted; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$ where Y=O, S or $H_2$, where $R^6$ is chosen from H, $C_{1-7}$-alkyl, saturated or unsaturated, branched or unbranched, mono- or polysubstituted or unsubstituted; or C(O)O—$C_{1-6}$-alkyl, saturated or unsaturated, branched or unbranched, mono- or polysubstituted or unsubstituted;

and where R7 is chosen from

H; $C_{3-8}$-cycloalkyl, aryl or heteroaryl, in each case unsubstituted or mono- or polysubstituted, where $R^8$ is chosen from aryl or heteroaryl, in each case unsubstituted or mono- or polysubstituted, where L is chosen from —C(O)—NH—, —NH—C(O)—, —C(O)—O—, —O—C(O)—, —O—, —S— or —S(O)$_2$— where $R^9$ is chosen from aryl or heteroaryl, in each case unsubstituted or mono- or polysubstituted, and $S^1$ and $S^2$ independently of one another are chosen from protective groups or together denote a protective group, preferably monoacetal.

In respect of the particularly suitable process described, it is particularly preferable if the protective groups on H in $R^{01}$, $R^{02}$, $R^{04}$ and/or $R^{05}$ are chosen from alkyl, benzyl or carbamates, for example, or fluorenylmethyl-chloroformate (FMOC) groups, benzyloxycarbonyl (Z) groups or tert-butyloxycarbonyl (Boc) groups.

Certain embodiments of the invention are explained further by the following, which are provided for purposes of explanation and illustration only and are not intended to, and should not be deemed to, limit the scope of the claims appended hereto.

EXAMPLES

The following examples show compounds according to certain embodiments of the invention and the preparation thereof and activity investigations carried out with these.

The following information generally applies here.

The chemicals and solvents employed were obtained commercially from the conventional suppliers (Acros, Avocado, Aldrich, Fluka, Lancaster, Maybridge, Merck, Sigma, TCI etc.) or were synthesized.

The analysis was carried out via NMR spectroscopy, optionally in combination with other analytical methods, such as thin layer chromatography, mass spectrometry or HPLC.

Example 1

General Possibility for the Preparation of Compounds According to the Invention

The preparation of these compounds is carried out starting from a cyclohexane-1,4-dione II suitably protected as, for example, the monoacetal. By reaction with potassium cyanide in the presence of a secondary amine, a protected N-substituted 1-amino-4-oxo-cyclohexanecarbonitrile derivative III is obtained.

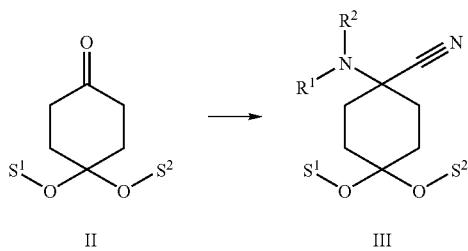

The reaction of the aminonitrile III with organometallic reagents, preferably Grignard or organolithium reagents, effects substitution of the nitrile function, so that after subsequent removal of the carbonyl protective group a 4-substituted 4-aminocyclohexanone derivative IV is obtained.

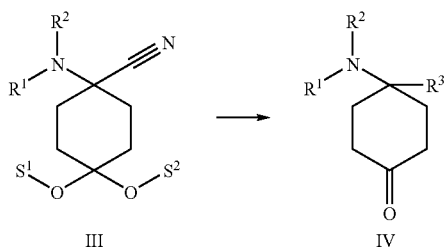

Intermediates of the type IV finally can be converted into 4-aminocyclohexanol derivatives I according to the invention by addition of organometallic reagents, preferably Grignard or organolithium reagents.

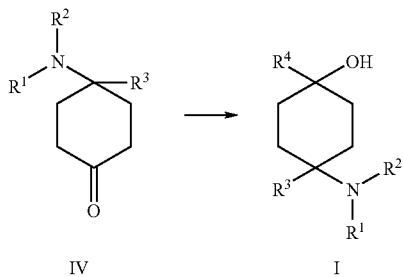

Example 2

Measurement of the ORL1 Binding

The 4-aminocyclohexanol derivatives of the general formula I were investigated in a receptor binding assay with $^3$H-nociceptin/orphanin FQ with membranes of recombinant CHO-ORL1 cells. This test system was carried out in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with in each case 20 µg membrane protein per 200 µl batch in 50 mM Hepes, pH 7.4, 10 mM MgCl$_2$ and 1 mM EDTA. The binding to the ORL1 receptor was determined using in each case 1 mg WGA-SPA Beads (Amersham-Pharmacia, Freiburg) by incubation of the batch for one hour at room temperature and subsequent measurement in the scintillation counter Trilux (Wallac, Finland). The affinity is stated as the $K_i$ value.

| Example No. | $K_i$ value (in µmol) |
|---|---|
| 4 | 0.02 |
| 5 | |
| 6 | 0.03 |
| 7 | 0.04 |
| 8 | 0.05 |
| 9 | 0.03 |
| 10 | 0.20 |
| 11 | 0.02 |
| 12 | |
| 13 | 0.06 |
| 14 | 0.90 |
| 15 | 0.40 |
| 16 | 0.89 |
| 17 | 0.04 |
| 18 | 0.13 |
| 19 | 0.045 |
| 20 | 0.15 |
| 21 | 0.15 |

Example 3

Analgesia Testing in the Tail Flick Test on the Mouse

The analgesic activity of the compounds according to the invention was investigated in the burning ray (tail flick) test on the mouse by the method of D'Amour and Smith (J. Pharm. Exp. Ther. 72, 74 79 (1941). NMRI mice weighing between 20-24 g were used for this. The animals were placed individually in special test cages and the base of the tail was exposed to a focused ray of heat from an electric lamp (tail flick type 55/12/10. fl, Labtec, Dr. Hess). The lamp intensity was adjusted such that the time from switching on the lamp to sudden jerking away of the tail (pain latency) was 3-5 seconds in untreated animals. Before administration of a compound according to the invention, the animals were pretested twice in the course of five minutes and the mean of these measurements was calculated as the pretest mean. The pain measurement was carried out 20, 40 and 60 min after intravenous administration. The analgesic action was determined as the increase in the pain latency (% MPE) according to the following formula:

$$[(T_1-T_0)/(T_2-T_0)] \times 100$$

In this, $T_0$ is the latency time before and $T_1$ the latency time after administration of the substance, $T_2$ is the maximum exposure time (12 sec).

To determine the dose dependency, the particular compound according to the invention was administered in 3-5 logarithmically increasing doses, which each included the threshold dose and the maximum active dose, and the $ED_{50}$ values were determined with the aid of regression analysis. The $ED_{50}$ calculation was performed in the action maximum 20 minutes after intravenous administration of the substance.

The compounds according to the invention investigated showed a pronounced analgesic action. The results are summarized in the following table.

| Example No. | % MPE (dosage in mg/kg intravenously) | ED$_{50}$ mg/kg intravenously |
| --- | --- | --- |
| 4 | 100 (1) | 0.015 |
| 5 | 100 (1) | 0.040 |
| 6 | 98 (1) | 0.055 |
| 7 | 93 (1) | 0.10 |
| 8 | 97 (1) | 0.093 |
| 9 | 100 (1) | 0.089 |
| 10 | 97 (1) | 0.16 |
| 11 | 99 (1) | 0.059 |
| 12 | 90 (1) | |
| 13 | 97 (10) | |
| 14 | 78 (1) | |
| 15 | 92 (1) | |
| 16 | 100 (1) | 0.028 |
| 17 | 100 (1) | 0.15 |
| 18 | 63 (10) | |
| 19 | 100 (1) | 0.04 |

Example 4

4-Benzyl-4-dimethylamino-1-phenethylcyclohexanol hydrochloride 200 g 1,4-dioxaspiro[4.5]decan-8-one were initially introduced into the reaction vessel, 1.68 l aqueous dimethylamine solution (40 per cent by volume), 200 ml methanol, 200 g potassium cyanide and 303 g dimethylamine hydrochloride were added in succession and the reaction mixture was stirred for 65 hours at room temperature. The white suspension obtained was extracted four times with 800 ml diethyl ether each time, the combined extracts were first concentrated and the residue was taken up in 500 ml methylene chloride, the organic phase was separated, dried over sodium sulfate, filtered and concentrated and the residue was largely freed from solvent residues in vacuo. 265 g 8-dimethylamino-1,4-dioxaspiro[4.5]decane-8-carbonitrile were obtained as a white solid.

50 g 8-dimethylamino-1,4-dioxaspiro[4.5]decane-8-carbonitrile were dissolved in 400 ml analytical grade tetrahydrofuran, 214 ml 2.0 molar benzylmagnesium chloride solution in THF were added under a nitrogen atmosphere and the mixture was stirred overnight at room temperature. For working up, 200 ml saturated ammonium chloride solution were added, while cooling with ice, the phases were separated, the aqueous phase was extracted twice with 250 ml diethyl ether each time, the combined organic phases were dried over sodium sulfate, filtered and concentrated and the residue was largely freed from solvent residues in vacuo. The crude (8-benzyl-1,4-dioxaspiro[4.5]dec-8-yl)-dimethylamine obtained (78.4 g) was stirred, without further purification, with a mixture of 200 ml conc. hydrochloric acid (32 per cent by weight) and 120 ml water for 24 hours at room temperature. The reaction mixture was then first washed three times with 100 ml diethyl ether each time, then rendered alkaline by addition of sodium hydroxide solution (32 per cent by weight), while cooling with ice, and extracted three times with 100 ml methylene chloride each time, the combined methylene chloride extracts were dried over sodium sulfate, filtered and concentrated and the residue was largely freed from solvent residues in vacuo. 50.4 g 4-benzyl-4-dimethylaminocyclohexanone were obtained as a brownish solid.

25.0 g 4-benzyl-4-dimethylaminocyclohexanone were dissolved in 150 ml analytical grade tetrahydrofuran, 151 ml 1.0 molar phenethylmagnesium chloride solution in THF were added under a nitrogen atmosphere, while cooling in an ice-bath, and the mixture was stirred overnight at room temperature. For working up, 150 ml ammonium chloride solution (20 per cent by weight) were added, while cooling with ice, the phases were separated, the aqueous phase was extracted three times with 80 ml diethyl ether each time, the combined organic phases were extracted three times with 70 ml dilute hydrochloric acid (5 per cent by weight) each time, the combined aqueous extracts were washed with 50 ml diethyl ether, adjusted to pH 9 with ammonia solution (25 per cent by weight) and extracted three times with 80 ml methylene chloride each time, the combined methylene chloride extracts were dried over sodium sulfate, filtered and concentrated and the residue was largely freed from solvent residues in vacuo. The crude product obtained (32.6 g) was chromatographed over silica gel with diethyl ether/hexane (v/v=1:1). 3.5 g of the nonpolar diastereoisomer of 4-benzyl-4-dimethylamino-1-phenethylcyclohexanol obtained were dissolved in 28 ml 2-butanone, 103 µl water followed by 1.44 ml trimethylchlorosilane were added at room temperature and the mixture was stirred over night at room temperature. The white solid which had precipitated out was filtered with suction, washed with diethyl ether and dried in an oil pump vacuum. 2.47 g of the hydrochloride of the nonpolar diastereoisomer of 4-benzyl-4-dimethylamino-1-phenethylcyclohexanol were obtained.

Example 5

4-Dimethylamino-1,4-diphenethylcyclohexanol hydrochloride 45 g 8-dimethylamino-1,4-dioxaspiro[4.5]decane-8-carbonitrile were dissolved in 250 ml analytical grade tetrahydrofuran, 238 ml 1.0 molar phenethylmagnesium chloride solution in THF were added under a nitrogen atmosphere and the mixture was stirred overnight at room temperature. For working up, 100 ml ammonium chloride solution (20 per cent by weight) were added, while cooling with ice, the phases were separated, the aqueous phase was extracted twice with 200 ml diethyl ether each time, the combined organic phases were washed successively with 100 ml water and 100 saturated sodium chloride solution, dried over sodium sulfate, filtered and concentrated and the residue was largely freed from solvent residues in vacuo. The crude dimethyl-(8-phenethyl-1,4-dioxa-spiro[4.5]dec-8-yl)-amine obtained as a yellow oil (54.1 g) was stirred, without further purification, with a mixture of 120 ml conc. hydrochloric acid (32 per cent by weight) and 70 ml water for 24 hours at room temperature. The reaction mixture was then first washed three times with 50 ml diethyl ether each time, then rendered alkaline by addition of sodium hydroxide solution (32 per cent by weight), while cooling with ice, and extracted three times with 100 ml methylene chloride each time, the combined methylene chloride extracts were dried over sodium sulfate, filtered and concentrated and the residue was largely freed from solvent residues in vacuo. 35.7 g of crude 4-dimethylamino-4-phenethyl-cyclohexanone were obtained as a slowly crystallizing brown oil.

7.58 g 4-dimethylamino-4-phenethylcyclohexanone were dissolved in 45 ml analytical grade tetrahydrofuran, 43 ml 1.0 molar phenethylmagnesium chloride solution in THF were added under a nitrogen atmosphere, while cooling in an ice-bath, and the mixture was stirred overnight at room temperature. For working up, 43 ml ammonium chloride solution (20 per cent by weight) were added, while cooling with ice, and the mixture was extracted three times with 80 ml diethyl ether each time, the combined organic phases were extracted three times with 70 ml dilute hydrochloric acid (5 per cent by weight) each time, the combined aqueous extracts were washed with 50 ml diethyl ether, adjusted to pH 9 with ammonia solution (25 per cent by weight) and extracted three times with 80 ml methylene chloride each time, the combined methylene chloride extracts were dried over sodium sulfate, filtered and concentrated and the residue was largely freed from solvent residues in vacuo. The crude product obtained (9.57 g) was chromatographed over silica gel with diethyl ether/hexane (v/v=1:1). 938 mg of the nonpolar diastereoisomer of 4-dimethylamino-1,4-diphenethylcyclohexanol obtained were dissolved in 7.5 ml 2-butanone, 26 μl water followed by 371 μl trimethylchlorosilane were added at room temperature and the mixture was stirred overnight at room temperature. The white solid which had precipitated out was filtered with suction, washed with diethyl ether and dried in an oil pump vacuum. 1.00 g of the hydrochloride of the nonpolar diastereoisomer of 4-dimethylamino-1,4-diphenethylcyclohexanol were obtained.

Example 6

4-Benzyl-4-dimethylamino-1-[2-(2-fluoroiphenyl) ethyl]cyclohexanol hydrochloride 11.4 g lithium aluminum hydride were initially introduced into 100 ml analytical grade tetrahydrofuran, the mixture was heated to the reflux temperature under a nitrogen atmosphere, 50 g 2-fluorophenylacetic acid, dissolved in 400 ml analytical grade tetrahydrofuran, were added dropwise and the reaction mixture was heated for a further two hours. For working up, 72 ml water followed by 250 ml half-concentrated hydrochloric acid (16 per cent by weight) were added dropwise, while cooling in an ice-bath. The mixture was extracted twice with 250 ml diethyl ether each time, the combined extracts were washed twice with 100 ml sodium bicarbonate solution (5 per cent by weight) each time, dried over sodium sulfate, filtered and concentrated and the residue was largely freed from solvent residues in vacuo. 40.2 g 2-(2-fluorophenyl)ethanol were obtained.

50 g 2-(2-fluorophenyl)ethanol, 19 ml concentrated sulfuric acid and 58 ml aqueous hydrobromic acid (47 per cent by weight) were heated at 100° C. overnight in a high-grade steel autoclave. After cooling, the mixture was diluted with 500 ml water and extracted twice with 250 ml methylene chloride each time, the combined extracts were dried over potassium carbonate, filtered and concentrated and the residue was largely freed from solvent residues in vacuo. 61.8 g 1-(2-bromoethyl)-2-fluorobenzene were obtained.

624 mg magnesium were stirred into 13 ml analytical grade tetrahydrofuran under a nitrogen atmosphere and approximately one third of the solution of 4.69 g 1-(2-bromoethyl)-2-fluorobenzene in 13 ml analytical grade tetrahydrofuran was added. The remainder of the solution was rapidly added dropwise after the Grignard formation had started, and when the addition had ended the mixture was subsequently stirred for one hour, 2.97 g 4-benzyl-4-dimethylaminocyclohexanone, dissolved in 13 ml analytical grade tetrahydrofuran, were then added dropwise and the reaction mixture was stirred overnight. For working up, 26 ml ammonium chloride solution (20 per cent by weight) were added, while cooling with ice, the phases were separated, the aqueous phase was extracted twice with 40 ml diethyl ether each time, the combined organic phases were washed with 50 ml water and extracted three times with 40 ml dilute hydrochloric acid (5 per cent by weight) each time, the combined aqueous extracts were washed with 30 ml diethyl ether, adjusted to pH 9 with ammonia solution (25 per cent by weight) and extracted three times with 40 ml methylene chloride each time, the combined methylene chloride extracts were dried over sodium sulfate, filtered and concentrated and the residue was largely freed from solvent residues in vacuo. The crude product obtained (4.39 g) was chromatographed over silica gel with diethyl ether/hexane (v/v=1:1). 1.50 g of the nonpolar diastereoisomer of 4-benzyl-4-dimethylamino-1-[2-(2-fluorophenyl) ethyl]cyclohexanol were obtained, from which 1.56 g of the corresponding hydrochloride were prepared as described for example 4.

Example 7

4-Benzyl-4-dimethylamino-1-[2-(4-fluorophenyl) ethyl]cyclohexanol hydrochloride 1-(2-Bromoethyl)-4-fluorobenzene was prepared from 4-fluorophenylacetic acid as described above for 1-(2-bromoethyl)-2-fluorobenzene.

841 mg magnesium were stirred into 17 ml analytical grade tetrahydrofuran under a nitrogen atmosphere and approximately one third of the solution of 6.32 g 1-(2-bromoethyl)-2-fluorobenzene in 17 ml analytical grade tetrahydrofuran was added. The remainder of the solution was rapidly added dropwise after the Grignard formation had started, and when the addition had ended the mixture was subsequently stirred for one hour, 4.00 g 4-benzyl-4-dimethylaminocyclohexanone, dissolved in 17 ml analytical grade tetrahydrofuran, were then added dropwise and the reaction mixture was stirred overnight. For working up, 35 ml ammonium chloride solution (20 per cent by weight) were added, while cooling with ice, the phases were separated, the aqueous phase was extracted twice with 40 ml diethyl ether each time, the combined organic phases were washed with 50 ml water and extracted three times with 40 ml dilute hydrochloric acid (5 per cent by weight) each time, the combined aqueous extracts were washed with 30 ml diethyl ether, adjusted to pH 9 with ammonia solution (25 per cent by weight) and extracted three times with 40 ml methylene chloride each time, the combined methylene chloride extracts were dried over sodium sulfate, filtered and concentrated and the residue was largely freed from solvent residues in vacuo. The crude product obtained (4.39 g) was chromatographed over silica gel. 1.08 g of the nonpolar diastereoisomer of 4-benzyl-4-dimethylamino-1-[2-(4-fluorophenyl)ethyl]cyclohexanol were obtained, from which 1.10 g of the corresponding hydrochloride were prepared as described for example 4.

Example 8

4-Dimethylamino-4-(2-fluorobenzyl)-1-phenethylcyclohexanol hydrochloride 1.16 g magnesium were stirred into 20 ml analytical grade diethyl ether under a nitrogen atmosphere and approximately one third of the solution of 6.19 g 2-fluorobenzyl chloride in 25 ml analytical grade diethyl ether was added. The remainder of the solution was rapidly added dropwise after the Grignard formation had started, and when the addition had ended the mixture was subsequently stirred for one hour, a solution of 5.00 g 8-dimethylamino-1,4-dioxaspiro[4.5]decane-8-carbonitrile in 25 ml analytical grade diethyl ether was then added dropwise and the reaction mixture was stirred overnight. For working up, 36 ml ammonium chloride solution (20 per cent by weight) were added, while cooling with ice, the phases were separated, the aqueous phase was extracted twice with 50 ml diethyl ether each time and the combined organic phases were washed successively with 20 ml water and 20 ml saturated sodium chloride solution. The crude [8-(2-fluorobenzyl)-1,4-dioxaspiro[4.5]dec-8-yl]dimethylamine obtained (7.34 g) was stirred, without further purification, with a mixture of 18 ml conc. hydrochloric acid (32 per cent by weight) and 10 ml water for 24 hours at room temperature. The reaction mixture was then first washed three times with 50 ml diethyl ether each time and then adjusted to pH 9 by addition of aqueous ammonia (25 per cent by weight), while cooling with ice, and extracted three times with 50 ml methylene chloride each time, the combined methylene chloride extracts were dried over sodium sulfate, filtered and concentrated and the residue was largely freed from solvent residues in vacuo. 5.80 g 4-dimethylamino-4-(2-fluorobenzyl)cyclohexanone were obtained as a yellow solid.

5.79 g 4-dimethylamino-4-(2-fluorobenzyl)cyclohexanone were dissolved in 35 ml analytical grade tetrahydrofuran, 42 ml 1.0 molar phenethylmagnesium chloride solution in THF were added under a nitrogen atmosphere, while cooling in an ice-bath, and the mixture was stirred overnight at room temperature. For working up, 42 ml ammonium chloride solution (20 per cent by weight) were added, while cooling with ice, the phases were separated, the aqueous phase was extracted three times with 50 ml diethyl ether each time, the combined organic phases were washed with 30 ml water and extracted three times with 50 ml dilute hydrochloric acid (5 per cent by weight) each time, the combined aqueous extracts were washed with 50 ml diethyl ether, adjusted to pH 9 with ammonia solution (25 per cent by weight) and extracted three times with 50 ml methylene chloride each time, the combined methylene chloride extracts were dried over sodium sulfate, filtered and concentrated and the residue was largely freed from solvent residues in vacuo. The crude product obtained (7.76 g) was chromatographed over silica gel with diethyl ether/hexane (v/v=1:1). 1.33 g of the nonpolar diastereoisomer of 4-dimethylamino-4-(2-fluorobenzyl)-1-phenethylcyclohexanol were obtained, from which 536 mg of the corresponding hydrochloride were prepared as described for example 4.

Example 9

4-Dimethylamino-4-(3-fluorobenzyl)-1-phenethylcyclohexanol hydrochloride 925 mg magnesium were stirred into 19 ml analytical grade diethyl ether under a nitrogen atmosphere and approximately one third of the solution of 4.95 g 3-fluorobenzyl chloride in 19 ml analytical grade diethyl ether was added. The remainder of the solution was rapidly added dropwise after the Grignard formation had started, and when the addition had ended the mixture was subsequently stirred for one hour, a solution of 4.00 g 8-dimethylamino-1,4-dioxaspiro[4.5]decane-8-carbonitrile in 25 ml analytical grade diethyl ether was then added dropwise and the reaction mixture was stirred overnight. For working up, 29 ml ammonium chloride solution (20 per cent by weight) were added, while cooling with ice, the phases were separated, the aqueous phase was extracted twice with 50 ml diethyl ether each time and the combined organic phases were washed successively with 20 ml water and 20 ml saturated sodium chloride solution. The crude [8-(3-fluorobenzyl)-1,4-dioxaspiro[4.5]dec-8-yl]dimethylamine obtained (5.75 g of yellow solid) was stirred, without further purification, with a mixture of 14 ml conc. hydrochloric acid (32 per cent by weight) and 8 ml water for 24 hours at room temperature. The reaction mixture was then first washed three times with 30 ml diethyl ether each time and then adjusted to pH 9 by addition of aqueous ammonia (25 per cent by weight), while cooling with ice, and extracted three times with 40 ml methylene chloride each time, the combined methylene chloride extracts were dried over sodium sulfate, filtered and concentrated and the residue was largely freed from solvent residues in vacuo. 4.71 g 4-dimethylamino-4-(3-fluorobenzyl)cyclohexanone were obtained as a yellow solid.

4.67 g 4-dimethylamino-4-(3-fluorobenzyl)cyclohexanone were dissolved in 28 ml analytical grade tetrahydrofuran, 34 ml 1.0 molar phenethylmagnesium chloride solution in THF were added under a nitrogen atmosphere, while cooling in an ice-bath, and the mixture was stirred overnight at room temperature. For working up, 34 ml ammonium chloride solution (20 per cent by weight) were added, while cooling with ice, the phases were separated, the aqueous phase was extracted three times with 40 ml diethyl ether each time, the combined organic phases were washed with 25 ml water and extracted three times with 40 ml dilute hydrochloric acid (5 per cent by weight) each time, the combined aqueous extracts were washed with 25 ml diethyl ether, adjusted to pH 9 with ammonia solution (25 per cent by weight) and extracted three times with 40 ml methylene chloride each time, the combined methylene chloride extracts were dried over sodium sulfate, filtered and concentrated and the residue was largely freed from solvent residues in vacuo. The crude product obtained (6.12 g of yellow resin) was chromatographed over silica gel with diethyl ether/hexane (v/v=1:1). 1.28 g of the nonpolar diastereoisomer of 4-dimethylamino-4-(3-fluorobenzyl)-1-phenethylcyclohexanol were obtained, from which 1.30 g of the corresponding hydrochloride were prepared as described for example 4.

Example 10

4-Dimethylamino-4-(4-fluorobenzyl)-1-phenethylcyclohexanol hydrochloride 925 mg magnesium were stirred into 19 ml analytical grade diethyl ether under a nitrogen atmosphere and approximately one third of the solution of 4.95 g 4-fluorobenzyl chloride in 19 ml analytical grade diethyl ether was added. The remainder of the solution was rapidly added dropwise after the Grignard formation had started, and when the addition had ended the mixture was subsequently stirred for one hour, a solution of 4.00 g 8-dimethylamino-1,4-dioxaspiro[4.5]decane-8-carbonitrile in 25 ml analytical grade diethyl ether was then added dropwise and the reaction mixture was stirred overnight. For working up, 29 ml ammonium chloride solution (20 per cent by weight) were added, while cooling with ice, the phases were separated, the aqueous phase was extracted twice with 50 ml diethyl ether each time and the combined organic phases were washed successively with 20 ml water and 20 ml saturated sodium chloride solution. The crude [8-(4-fluorobenzyl)-1,4-dioxaspiro[4.5]dec-8-yl]dimethylamine obtained (5.76 g of yellow solid) was stirred, without further purification, with a mixture of 14 ml conc. hydrochloric acid (32 per cent by weight) and 8 ml water for 24 hours at room temperature. The reaction mixture was then first washed three times with 30 ml diethyl ether each time and then adjusted to pH 9 by addition of aqueous ammonia (25 per cent by weight), while cooling with ice, and extracted three times with 40 ml methylene chloride each time, the combined methylene chloride extracts were dried over sodium sulfate, filtered and concentrated and the residue was largely freed from solvent residues in vacuo. 4.70 g 4-dimethylamino-4-(4-fluorobenzyl)cyclohexanone were obtained as a yellow solid.

4.69 g 4-dimethylamino-4-(4-fluorobenzyl)cyclohexanone were dissolved in 28 ml analytical grade tetrahydrofuran, 34 ml 1.0 molar phenethylmagnesium chloride solution in THF were added under a nitrogen atmosphere, while cooling in an ice-bath, and the mixture was stirred overnight at room temperature. For working up, 34 ml ammonium chloride solution (20 per cent by weight) were added, while cooling with ice, the phases were separated, the aqueous phase was extracted three times with 40 ml diethyl ether each time, the combined organic phases were washed with 25 ml water and extracted three times with 40 ml dilute hydrochloric acid (5 per cent by weight) each time, the combined aqueous extracts were washed with 25 ml diethyl ether, adjusted to pH 9 with ammonia solution (25 per cent by weight) and extracted three times with 40 ml methylene chloride each time, the combined methylene chloride extracts were dried over sodium sulfate, filtered and concentrated and the residue was largely freed from solvent residues in vacuo. The crude product obtained (6.40 g of yellow resin) was chromatographed over silica gel with diethyl ether/hexane (v/v=1:1). 1.45 g of the nonpolar diastereoisomer of 4-dimethylamino-4-(4-fluorobenzyl)-1-phenethylcyclohexanol were obtained, from which 1.44 g of the corresponding hydrochloride were prepared as described for example 4.

Example 11

4-Benzyl-4-dimethylamino-1-[2-(4-fluorophenyl)ethyl]cyclohexanol hydrochloride 1-(2-Bromoethyl)-3-fluorobenzene was prepared from 3-fluorophenylacetic acid as described above for 1-(2-bromoethyl)-2-fluorobenzene.

757 mg magnesium were stirred into 15 ml analytical grade tetrahydrofuran under a nitrogen atmosphere and approximately one third of the solution of 5.69 g 1-(2-bromoethyl)-3-fluorobenzene in 16 ml analytical grade tetrahydrofuran was added. The remainder of the solution was rapidly added dropwise after the Grignard formation had started, and when the addition had ended the mixture was subsequently stirred for one hour, 3.60 g 4-benzyl-4-dimethylaminocyclohexanone, dissolved in 16 ml analytical grade tetrahydrofuran, were then added dropwise and the reaction mixture was stirred overnight. For working up, 31 ml ammonium chloride solution (20 per cent by weight) were added, while cooling with ice, the phases were separated, the aqueous phase was extracted twice with 40 ml diethyl ether each time, the combined organic phases were washed with 30 ml water and extracted three times with 40 ml dilute hydrochloric acid (5 per cent by weight) each time, the combined aqueous extracts were washed with 30 ml diethyl ether, adjusted to pH 9 with ammonia solution (25 per cent by weight) and extracted three times with 40 ml methylene chloride each time, the combined methylene chloride extracts were dried over sodium sulfate, filtered and concentrated and the residue was largely freed from solvent residues in vacuo. The crude product obtained (3.96 g) was chromatographed over silica gel with diethyl ether/hexane (v/v=1:1). 301 mg of the nonpolar diastereoisomer of 4-benzyl-4-dimethylamino-1[2-(4-fluorophenyl)ethyl]cyclohexanol were obtained, from which 254 mg of the corresponding hydrochloride were prepared as described for example 4.

Example 12

4-Benzyl-4-dimethylamino-1-(2-fluorobenzyl)cyclohexanol hydrochloride 757 mg magnesium were stirred into 15 ml analytical grade diethyl ether under a nitrogen atmosphere and approximately one third of the solution of 4.05 g 2-fluorobenzyl chloride in 15 ml analytical grade diethyl ether was added. The remainder of the solution was rapidly added dropwise after the Grignard formation had started, and when the addition had ended the mixture was subsequently stirred for one hour, 3.60 g 4-benzyl-4-dimethylaminocyclohexanone, dissolved in 40 ml analytical grade diethyl ether, were then added dropwise and the reaction mixture was stirred overnight. For working up, 31 ml ammonium chloride solution (20 per cent by weight) were added, while cooling with ice, the phases were separated, the aqueous phase was extracted twice with 40 ml diethyl ether each time, the combined organic phases were washed with 30 ml water and extracted three times with 40 ml dilute hydrochloric acid (5 per cent by weight) each time, the combined aqueous extracts were washed with 30 ml diethyl ether, adjusted to pH 9 with ammonia solution (25 per cent by weight) and extracted three times with 40 ml methylene chloride each time, the combined methylene chloride extracts were dried over sodium sulfate, filtered and concentrated and the residue was largely freed from solvent residues in vacuo. The crude product obtained (5.02 g) was chromatographed over silica gel with diethyl ether/hexane (v/v=1:1). 2.44 g of the nonpolar diastereoisomer of 4-benzyl-4-dimethylamino-1-(2-fluorobenzyl)cyclohexanol were obtained, from which 2.53 g of the corresponding hydrochloride were prepared as described for example 4.

Example 13

4-(Allylmethylamino)-4-benzyl-1-phenethylcyclohexanol hydrochloride

A mixture of 9 ml water, 5.3 ml hydrochloric acid (32 per cent by weight), 8 ml methanol, 17.5 g allylmethylamine, 8.00 g 1,4-dioxaspiro[4.5]decan-8-one and 8.0 g potassium cyanide was stirred for 65 hours at room temperature. The yellowish-white suspension obtained was extracted four times with 25 ml diethyl ether each time, the combined extracts were dried over sodium sulfate, filtered and concentrated and the residue was largely freed from solvent residues in vacuo. 11.3 g 8-(allylmethylamino)-1,4-dioxaspiro[4.5]decane-8-carbonitrile were obtained as a pale brown liquid.

A solution of 3.50 g 8-(allylmethylamino)-1,4-dioxaspiro[4.5]decane-8-carbonitrile in 35 ml analytical grade tetrahydrofuran was added dropwise to 14.8 ml 2.0 molar benzylmagnesium chloride solution in THF under a nitrogen atmosphere and the mixture was stirred overnight at room temperature. For working up, 25 ml saturated ammonium chloride solution were added, while cooling with ice, the phases were separated, the aqueous phase was extracted three times with 25 ml diethyl ether each time, the combined organic phases were dried over sodium sulfate, filtered and concentrated and the residue was largely freed from solvent residues in vacuo. The crude allyl-(8-benzyl-1,4-dioxaspiro[4.5]dec-8-yl)methylamine obtained (5.41 g) was stirred, without further purification, with a mixture of 13 ml conc. hydrochloric acid (32 per cent by weight) and 7.5 ml water for 24 hours at room temperature. The reaction mixture was then first washed three times with 50 ml diethyl ether each time and then rendered alkaline by addition of sodium hydroxide solution (32 per cent by weight), while cooling with ice, and extracted three times with 100 ml methylene chloride each time, the combined methylene chloride extracts were dried over sodium sulfate, filtered and concentrated and the residue was largely freed from solvent residues in vacuo. 3.55 g 4-(allylmethylamino)-4-benzylcyclohexanone were obtained.

A solution of 3.50 g 4-(allylmethylamino)-4-benzylcyclohexanone in 21 ml analytical grade tetrahydrofuran was added dropwise to 14.8 ml 1.0 molar phenethylmagnesium chloride solution in THF under a nitrogen atmosphere and the mixture was stirred overnight at room temperature. For working up, 19 ml ammonium chloride solution (20 per cent by weight) were added, while cooling with ice, the phases were separated, the aqueous phase was extracted three times with 20 ml diethyl ether each time, the combined organic phases were washed with 20 ml water and extracted three times with 20 ml dilute hydrochloric acid (5 per cent by weight) each time, the combined aqueous extracts were washed with 20 ml diethyl ether, adjusted to pH 9 with ammonia solution (25 per cent by weight) and extracted three times with 50 ml methylene chloride each time, the combined methylene chloride extracts were dried over sodium sulfate, filtered and concentrated and the residue was largely freed from solvent residues in vacuo. The crude product obtained (4.00 g of brown resin) was chromatographed over silica gel with diethyl ether/hexane (v/v=1:1). 2.04 g of the nonpolar diastereoisomer of 4-(allylmethylamino)-4-benzyl-1-phenethylcyclohexanol were obtained, from which 807 mg of the corresponding hydrochloride were prepared as described for example 4.

Example 14

4-Benzyl-4-dimethylamino-1-(3-fluorobenzyl)cyclohexanol hydrochloride 757 mg magnesium were stirred into 15 ml analytical grade diethyl ether under a nitrogen atmosphere and approximately one third of the solution of 4.05 g 3-fluorobenzyl chloride in 15 ml analytical grade diethyl ether was added. The remainder of the solution was rapidly added dropwise after the Grignard formation had started, and when the addition had ended the mixture was subsequently stirred for one hour, 3.60 g 4-benzyl-4-dimethylaminocyclohexanone, dissolved in 30 ml analytical grade diethyl ether, were then added dropwise and the reaction mixture was stirred overnight. For working up, 31 ml ammonium chloride solution (20 per cent by weight) were added, while cooling with ice, the phases were separated, the aqueous phase was extracted twice with 40 ml diethyl ether each time, the combined organic phases were washed with 20 ml water and extracted three times with 40 ml dilute hydrochloric acid (5 per cent by weight) each time, the combined aqueous extracts were washed with 30 ml diethyl ether, adjusted to pH 9 with ammonia solution (25 per cent by weight) and extracted three times with 40 ml methylene chloride each time, the combined methylene chloride extracts were dried over sodium sulfate, filtered and concentrated and the residue was largely freed from solvent residues in vacuo. The crude product obtained (4.91 g of yellow resin) was chromatographed over silica gel with diethyl ether/hexane (v/v=1:1). 1.93 g of the nonpolar diastereoisomer of 4-benzyl-4-dimethylamino-1-(3-fluorobenzyl)cyclohexanol were obtained as a white solid, from which 2.09 g of the corresponding hydrochloride were prepared as described for example 4.

Example 15

4-Benzyl-4-dimethylamino-1-(4-fluorobenzyl)cyclohexanol hydrochloride 757 mg magnesium were stirred into 15 ml analytical grade diethyl ether under a nitrogen atmosphere and approximately one third of the solution of 4.05 g 4-fluorobenzyl chloride in 15 ml analytical grade diethyl ether was added. The remainder of the solution was rapidly added dropwise after the Grignard formation had started, and when the addition had ended the mixture was subsequently stirred for one hour, 3.60 g 4-benzyl-4-dimethylaminocyclohexanone, dissolved in 30 ml analytical grade diethyl ether, were then added dropwise and the reaction mixture was stirred overnight. For working up, 31 ml ammonium chloride solution (20 per cent by weight) were added, while cooling with ice, the phases were separated, the aqueous phase was extracted twice with 40 ml diethyl ether each time, the combined organic phases were washed with 20 ml water and extracted three times with 40 ml dilute hydrochloric acid (5 per cent by weight) each time, the combined aqueous extracts were washed with 30 ml diethyl ether, adjusted to pH 9 with ammonia solution (25 per cent by weight) and extracted three times with 40 ml methylene chloride each time, the combined methylene chloride extracts were dried over sodium sulfate, filtered and concentrated and the residue was largely freed from solvent residues in vacuo. The crude product obtained (5.08 g of yellow resin) was chromatographed over silica gel with diethyl ether/hexane (v/v=1:1). 2.24 g of the nonpolar diastereoisomer of 4-benzyl-4-dimethylamino-1-(4-fluorobenzyl)cyclohexanol were obtained as a white solid, from which 2.32 g of the corresponding hydrochloride were prepared as described for example 4.

Example 16

1-Benzyl-4-dimethylamino-4-(3-fluorobenzyl)cyclohexanol hydrochloride 925 mg magnesium were stirred into 19 ml analytical grade diethyl ether under a nitrogen atmosphere and approximately one third of the solution of 4.95 g 3-fluorobenzyl chloride in 19 ml analytical grade diethyl ether was added. The remainder of the solution was rapidly added dropwise after the Grignard formation had started, and when the addition had ended the mixture was subsequently stirred for one hour, a solution of 4.00 g 8-dimethylamino-1,4-dioxaspiro[4.5]decane-8-carbonitrile in 25 ml analytical grade diethyl ether was then added dropwise and the reaction mixture was stirred overnight. For working up, 29 ml ammonium chloride solution (20 per cent by weight) were added, while cooling with ice, the phases were separated, the aqueous phase was extracted twice with 50 ml diethyl ether each time and the combined organic phases were washed successively with 20 ml water and 20 ml saturated sodium chloride solution. The crude [8-(3-fluorobenzyl)-1,4-dioxaspiro[4.5]dec-8-yl]dimethylamine obtained (5.75 g of yellow solid) was stirred, without further purification, with a mixture of 14 ml conc. hydrochloric acid (32 per cent by weight) and 8 ml water for 24 hours at room temperature. The reaction mixture was then first washed three times with 30 ml diethyl ether each time and then adjusted to pH 9 by addition of aqueous ammonia (25 per cent by weight), while cooling with ice, and extracted three times with 40 ml methylene chloride each time, the combined methylene chloride extracts were dried over sodium sulfate, filtered and concentrated and the residue was largely freed from solvent residues in vacuo. 4.71 g 4-dimethylamino-4-(3-fluorobenzyl)cyclohexanone were obtained as a yellow solid.

4.67 g 4-dimethylamino-4-(3-fluorobenzyl)cyclohexanone were reacted with 1.0 molar benzylmagnesium chloride solution in THF analogously to the preparation of 4-dimethylamino-4-(4-fluorobenzyl)-1-phenethylcyclohexanol. After chromatography over silica gel, the nonpolar diastereoisomer of 1-benzyl-4-dimethylamino-4-(3-fluorobenzyl)cyclohexanol obtained was converted into 261 mg of the corresponding hydrochloride as described for example 4.

Example 17

4-Benzyl-1-phenethyl-4-pyrrolidin-1-ylcyclohexanol hydrochloride

A mixture of 55 ml water, 33 ml hydrochloric acid (32 per cent by weight), 50 ml methanol, 127 ml pyrrolidine, 50.0 g 1,4-dioxaspiro[4.5]decan-8-one and 50.0 g potassium cyanide was stirred for 65 hours at room temperature. The pale brown suspension obtained was extracted four times with 50 ml diethyl ether each time, the combined extracts were dried over sodium sulfate, filtered and concentrated and the residue was largely freed from solvent residues in vacuo. 76.7 g 8-pyrrolidin-1-yl-1,4-dioxaspiro[4.5]decane-8-carbonitrile were obtained as a pale brown liquid.

A solution of 40.0 g 8-pyrrolidin-1-yl-1,4-dioxaspiro[4.5]decane-8-carbonitrile in 150 ml analytical grade tetrahydrofuran was added dropwise to 127 ml 2.0 molar benzylmagnesium chloride solution in THF under a nitrogen atmosphere and the mixture was stirred overnight at room temperature. For working up, 50 ml saturated ammonium chloride solution were added, while cooling with ice, the phases were separated, the aqueous phase was extracted three times with 50 ml diethyl ether each time, the combined organic phases were dried over sodium sulfate, filtered and concentrated and the residue was largely freed from solvent residues in vacuo. The crude 1-(8-benzyl-1,4-dioxaspiro[4.5]dec-8-yl)pyrrolidine obtained (54.0 g of yellow solid) was stirred, without further purification, with a mixture of 128 ml conc. hydrochloric acid (32 per cent by weight) and 74 ml water for 24 hours at room temperature. The reaction mixture was then first washed twice with 50 ml diethyl ether each time and then rendered alkaline by addition of sodium hydroxide solution (32 per cent by weight), while cooling with ice, and extracted three times with 100 ml methylene chloride each time, the combined methylene chloride extracts were dried over sodium sulfate, filtered and concentrated and the residue was largely freed from solvent residues in vacuo. 40.3 g 4-benzyl-4-pyrrolidin-1-yl-cyclohexanone were obtained.

A solution of 4.00 g 4-benzyl-4-pyrrolidin-1-yl-cyclohexanone in 40 ml analytical grade tetrahydrofuran was added dropwise to 23.3 ml 1.0 molar phenethylmagnesium chloride solution in THF under a nitrogen atmosphere and while cooling in an ice-bath and the mixture was stirred overnight at room temperature. For working up, 25 ml ammonium chloride solution (20 per cent by weight) were added, while cooling with ice, the phases were separated, the aqueous phase was extracted three times with 50 ml diethyl ether each time, the combined organic phases were dried over sodium sulfate, filtered and concentrated and the residue was largely freed from solvent residues in vacuo. The crude product obtained (6.26 g of brown oil) was chromatographed over silica gel with methanol/ethyl acetate (v/v=1:1). 2.48 g of the nonpolar diastereoisomer of 4-benzyl-1-phenethyl-4-pyrrolidin-1-yl-cyclohexanol were obtained, from which 1.98 g of the corresponding hydrochloride were prepared as described for example 4.

Example 18

4-Benzyl-4-dimethylamino-1-(1-methyl-1H-indol-2-yl)cyclohexanol

A solution of N-methylindole (1.50 mg, 3.81 mmol) in dry THF (20 ml) was cooled to −5° C. under a stream of argon. Thereafter, tert-butyllithium (4.19 mmol, 2.47 ml of a 1.7 molar pentane solution) was added dropwise such that a reaction temperature of 0° C. was not exceeded during the addition. When the addition had ended the reaction mixture was stirred for a further two hours at 0° C. A solution of 4-benzyl-4-dimethylaminocyclohexanone (3.88 mg, 3.81 mmol) in dry THF (7 ml) was then added dropwise at 0° C. The mixture was stirred for 15 minutes at 0° C. and then for four hours at room temperature. The reaction mixture was quenched with saturated ammonium chloride solution (20 ml), the organic phase was separated and the aqueous phase was extracted four times with methylene chloride (20 ml). The combined organic phases were dried over sodium sulfate and filtered and the solvent was removed in vacuo. Purification was carried out by means of flash chromatography over silica gel with cyclohexane/ethyl acetate (v/v=4:1). 456 mg 4-benzyl-4-dimethylamino-1-(1-methyl-1H-indol-2-yl) cyclohexanol with a melting point of 105-107° C. were obtained.

Example 19

1-Benzo[b]thionhen-2-yl-4-benzyl-4-dimethylaminocyclohexanol

A solution of benzo[b]thiophene (1.50 mg, 3.73 mmol) in 20 ml dry THF was cooled to −5° C. under a stream of argon. tert-Butyllithium (4.47 mmol, 2.63 ml of a 1.7 molar pentane solution) was then added dropwise such that a reaction temperature of 0° C. was not exceeded during the addition. When the addition had ended the reaction mixture was stirred for two hours at 0° C. Thereafter, a solution of 4-benzyl-4-dimethylaminocyclohexanone (3.86 mg, 3.73 mmol) in dry THF (8 ml) was added dropwise at 0° C. The mixture was stirred for 15 minutes at 0° C. and then for five hours at room temperature. The reaction mixture was quenched with saturated ammonium chloride solution (30 ml), the organic phase was separated and the aqueous phase was extracted four times with methylene chloride (25 ml). The combined organic phases were dried over sodium sulfate and filtered and the solvent was removed in vacuo. Purification was carried out by means of flash chromatography over silica gel with cyclohexane/ethyl acetate (v/v=9:1). 517 mg 1-benzo[b]thiophen-2-yl-4-benzyl-4-dimethylaminocyclohexanol with a melting point of 128-131° C. were obtained.

Example 20

1-Benzo[b]thiophen-3-yl-4-benzyl-4-dimethylaminocyclohexanol

A solution of 3-bromo-1-benzo[b]thiophene (1.90 mg, 4.22 mmol) in 30 ml dry diethyl ether was cooled to −78° C. under a stream of argon. Thereafter, n-butyllithium (5.07 mmol, 3.17 ml of a 15 per cent by weight hexane solution) was cautiously added dropwise such that a reaction temperature of −75° C. was not exceeded during the addition. When the addition had ended the reaction mixture was stirred for two hours at −78° C. Thereafter, a solution of 4-benzyl-4-dimethylaminocyclohexanone (977 mg, 4.22 mmol) in dry diethyl ether (10 ml) was added dropwise at −78° C. The mixture was stirred for four hours at −78° C. and then thawed slowly to room temperature (approximately twelve hours). The reaction mixture was quenched with saturated ammonium chloride solution (30 ml), the organic phase was separated and the aqueous phase was extracted four times with methylene chloride (25 ml). The combined organic phases were dried over sodium sulfate and filtered and the solvent was removed in vacuo. Purification is carried out by means of flash chromatography over silica gel with cyclohexane/ethyl acetate (v/v=7:3). 324 mg 1-benzo[b]thiophen-3-yl-4-benzyl-4-dimethylaminocyclohexanol with a melting point of 158-160° C. were obtained.

Example 21

1-Benzofuran-2-yl-4-benzyl-4-dimethylaminocyclohexanol

A solution of benzo[b]furan (612 mg, 5.12 mmol) in dry THF (40 ml) was cooled to −8° C. under a stream of argon. Thereafter, tert-Butyllithium (6.22 mmol, 4.14 ml of a 1.5 molar pentane solution) was added dropwise such that a reaction temperature of −5° C. was not exceeded during the addition. When the addition had ended the reaction mixture was stirred for two hours at −5° C. Thereafter, a solution of 4-benzyl-4-dimethylaminocyclohexanone (1.20 g, 5.18 mmol) in dry THF (10 ml) was added dropwise at 0° C. The mixture was stirred for one hour at 0° C. and then for four days at room temperature. The reaction mixture was quenched with saturated ammonium chloride solution (20 ml), the organic phase was separated and the aqueous phase was extracted four times with 30 ml methylene chloride each time. The combined organic phases were dried over sodium sulfate and filtered and the solvent was removed in vacuo. Purification was carried out by means of flash chromatography over silica gel with cyclohexane/ethyl acetate (v/v=8:2). 380 mg 1-benzofuran-2-yl-4-benzyl-4-dimethylaminocyclohexanol with a melting point of 121-124° C. were obtained.

| Example No. | |
|---|---|
| 4 | 4-benzyl-4-dimethylamino-1-phenethylcyclohexanol hydrochloride |
| 5 | 4-dimethylamino-1,4-diphenethylcyclohexanol hydrochloride |
| 6 | 4-benzyl-4-dimethylamino-1-[2-(2-fluorophenyl)ethyl]cyclohexanol hydrochloride |
| 7 | 4-benzyl-4-dimethylamino-1-[2-(4-fluorophenyl)ethyl]cyclohexanol hydrochloride |
| 8 | 4-dimethylamino-4-(2-fluorobenzyl)-1-phenethylcyclohexanol hydrochloride |
| 9 | 4-dimethylamino-4-(3-fluorobenzyl)-1-phenethylcyclohexanol hydrochloride |
| 10 | 4-dimethylamino-4-(4-fluorobenzyl)-1-phenethylcyclohexanol hydrochloride |
| 11 | 4-benzyl-4-dimethylamino-1-[2-(3-fluorophenyl)ethyl]cyclohexanol hydrochloride |
| 12 | 4-benzyl-4-dimethylamino-1-(2-fluorobenzyl)cyclohexanol hydrochloride |
| 13 | 4-(allylmethylamino)-4-benzyl-1-phenethylcyclohexanol hydrochloride |
| 14 | 4-benzyl-4-dimethylamino-1-(3-fluorobenzyl)cyclohexanol hydrochloride |
| 15 | 4-benzyl-4-dimethylamino-1-(4-fluorobenzyl)cyclohexanol; hydrochloride |
| 16 | 1-benzyl-4-dimethylamino-4-(3-fluorobenzyl)cyclohexanol hydrochloride |
| 17 | 4-benzyl-1-phenethyl-4-pyrrolidin-1-ylcyclohexanol hydrochloride |
| 18 | 4-benzyl-4-dimethylamino-1-(1-methyl-1H-indol-2-yl)cyclohexanol |
| 19 | 1-benzo[b]thiophen-2-yl-4-benzyl-4-dimethylaminocyclohexanol |
| 20 | 1-benzo[b]thiophen-3-yl-4-benzyl-4-dimethylaminocyclohexanol |
| 21 | 1-benzofuran-2-yl-4-benzyl-4-dimethylamino-cyclohexanol |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A substituted 4-aminocyclohexanol compound corresponding to formula I,

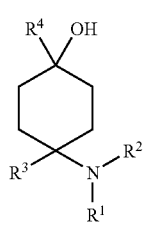

I wherein
R$^1$ and R$^2$ independently of one another represent H; C$_{1-8}$-alkyl or C$_{3-8}$-cycloalkyl, in each case saturated or unsaturated, branched or unbranched, mono- or polysubstituted or unsubstituted; aryl- or heteroaryl, in each case mono- or polysubstituted or unsubstituted; or aryl, C$_{3-8}$-cycloalkyl or heteroaryl bonded via C$_{1-3}$-alkylene and in each case mono- or polysubstituted or unsubstituted; wherein R$^1$ and R$^2$ are not both H, or the radicals R$^1$ and R$^2$ together form a ring and represent CH$_2$CH$_2$OCH$_2$CH$_2$, CH$_2$CH$_2$NR$^5$CH$_2$CH$_2$ or (CH$_2$)$_{3-6}$, wherein R$^5$ represents H; C$_{1-8}$-alkyl or C$_{3-8}$-cycloalkyl, in each case saturated or unsaturated, branched or unbranched, mono- or polysubstituted or unsubstituted; aryl- or heteroaryl, in each case mono- or polysubstituted or unsubstituted; or aryl, C$_{3-8}$-cycloalkyl or heteroaryl bonded via C$_{1-3}$-alkylene and in each case mono- or polysubstituted or unsubstituted;

R$^3$ represents C$_{1-8}$-alkyl or C$_{3-8}$-cycloalkyl, in each case saturated or unsaturated, branched or unbranched, mono- or polysubstituted or unsubstituted; or aryl, C$_{3-8}$-cycloalkyl or heteroaryl bonded via a saturated or unsaturated, branched or unbranched, substituted or unsubstituted C$_{1-4}$-alkyl group and in each case unsubstituted or mono- or polysubstituted;

R$^4$ represents C$_{3-8}$-cycloalkyl, aryl or heteroaryl, in each case unsubstituted or mono- or polysubstituted; —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$; or —R$^8$-L-R$^9$ wherein Y=O, S or H$_2$;

R$^6$ represents H; C$_{1-7}$-alkyl, saturated or unsaturated, branched or unbranched, mono- or polysubstituted or unsubstituted; or C(O)O—C$_{1-6}$-alkyl, saturated or unsaturated, branched or unbranched, mono- or polysubstituted or unsubstituted;

R$^7$ represents H; C$_{3-8}$-cycloalkyl, aryl or heteroaryl, in each case unsubstituted or mono- or polysubstituted;

R$^8$ represents aryl or heteroaryl, in each case unsubstituted or mono- or polysubstituted;

L represents —C(O)—NH—, —NH—C(O)—, —C(O)—O—, —O—C(O)—, —O—, —S— or —S(O)$_2$—; and R⁹ represents aryl or heteroaryl, in each case unsubstituted or mono- or polysubstituted, or a salt thereof with a physiologically tolerated acid.

2. The compound of claim 1, wherein said compound is in the form of a free base.

3. The compound of claim 1, wherein said compound is present in the form of a pure enantiomer or pure diastereoisomer.

4. The compound of claim 1, wherein said compound is present in the form of a mixture of stereoisomers.

5. The compound of claim 1, wherein said compound is present in the form of a racemic mixture.

6. The compound of claim 1, wherein said compound is present in the form of a solvate.

7. The compound of claim 1, wherein said compound is present in the form of a hydrate.

8. The compound of claim 1, wherein
$R^1$ and $R^2$ independently of one another represent H or
$C_{1-8}$-alkyl, saturated or unsaturated, branched or unbranched, mono- or polysubstituted or unsubstituted; wherein $R^1$ and $R^2$ are not both H, or $R^1$ and $R^2$ together form a ring and represent $CH_2CH_2OCH_2CH_2$, $CH_2CH_2NR^5CH_2CH_2$ or $(CH_2)_{3-6}$, wherein $R^5$ represents H or
$C_{1-8}$-alkyl, saturated or unsaturated, branched or unbranched, mono- or polysubstituted or unsubstituted.

9. The compound of claim 8, wherein:
$R^1$ and $R^2$ independently of one another represent H or
$C_{1-4}$-alkyl, saturated or unsaturated, branched or unbranched, mono- or polysubstituted or unsubstituted; where $R^1$ and $R^2$ are not both H, or $R^1$ and $R^2$ together form a ring and represent $(CH_2)_{4-5}$.

10. The compound of claim 9, wherein:
$R^1$ and $R^2$ independently of one another represent methyl or ethyl or $R^1$ and
$R^2$ together form a ring and represent $(CH_2)_5$.

11. The compound of claim 1, wherein:
$R^3$ represents $C_{3-8}$-cycloalkyl, unsubstituted or mono- or polysubstituted; or
aryl, $C_{3-8}$-cycloalkyl or heteroaryl bonded via a saturated or unsaturated, unbranched, substituted or unsubstituted $C_{1-4}$-alkyl group and in each case unsubstituted or mono- or polysubstituted.

12. The compound of claim 1, wherein:
$R^3$ represents $C_{5-6}$-cycloalkyl, unsubstituted or mono- or polysubstituted; or
$C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched $C_{1-2}$-alkyl group and in each case unsubstituted or mono- or polysubstituted.

13. The compound of claim 1, wherein:
$R^3$ represents phenyl, pyridyl, furyl or thiophenyl bonded via a saturated, unbranched $C_{1-2}$-alkyl group and in each case unsubstituted or mono- or polysubstituted.

14. The compound of claim 1, wherein:
$R^4$ represents $C_{3-8}$-cycloalkyl, aryl or heteroaryl, in each case unsubstituted or mono- or polysubstituted; or —$R^8$-L-$R^9$.

15. The compound of claim 1, wherein:
$R^4$ represents cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted; or —$R^8$-L-$R^9$.

16. The compound of claim 1, wherein:
$R^4$ represents cyclopentyl, cyclohexyl, cycloheptyl, cyclooctyl, anthracenyl, indolyl, naphthyl, benzothiazolyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted; or —$R^8$-L-$R^9$.

17. The compound of claim 1, wherein:
$R^8$ represents indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl, in each case unsubstituted or mono- or polysubstituted;

L represents —C(O)—NH—, —NH—C(O)—, —C(O)—O—, —O—C(O)—, —O—, —S— or —S(O)$_2$—;

or $R^9$ represents indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl, in each case unsubstituted or mono- or polysubstituted.

18. The compound of claim 1, wherein:
$R^8$ represents indolyl, benzothiophenyl, phenyl, thiophenyl, furyl, pyridyl, pyrrolyl, pyrazinyl or pyrimidyl, in each case unsubstituted or mono- or polysubstituted;

L represents —C(O)—NH—, —NH—C(O)—, —C(O)—O—, —O—C(O)— or —S(O)$_2$—;

or $R^9$ represents indolyl, benzothiophenyl, phenyl, thiophenyl, furyl, pyridyl, pyrrolyl, pyrazinyl or pyrimidyl, in each case unsubstituted or mono- or polysubstituted.

19. The compound of claim 1, wherein:
$R^8$ represents unsubstituted indolyl;
L represents —S(O)$_2$-; and
$R^9$ represents unsubstituted phenyl.

20. The compound of claim 1, wherein:
$R^4$ represents —CHR$^6$R$^7$, —CHR$^6$—CH$_2$R$^7$, —CHR$^6$—CH$_2$—CH$_2$R$^7$, —CHR$^6$—CH$_2$—CH$_2$—CH$_2$R$^7$, —C(Y)R$^7$, —C(Y)—CH$_2$R$^7$, —C(Y)—CH$_2$—CH$_2$R$^7$ or —C(Y)—CH$_2$—CH$_2$—CH$_2$R$^7$ and Y=O,S or H$_2$.

21. The compound of claim 1, wherein:
$R^4$ represents —CHR$^6$R$^7$, —CHR$^6$—CH$_2$R$^7$, —CHR$^6$—CH$_2$—CH$_2$R$^7$, —C(Y)R$^7$, —C(Y)—CH$_2$R$^7$ or —C(Y)—CH$_2$—CH$_2$R$^7$ and Y=O or S.

22. The compound of claim 1, wherein:
$R^4$ represents —CHR$^6$R$^7$, —CHR$^6$—CH$_2$R$^7$, —C(Y)R$^7$ or —C(Y)—CH$_2$R$^7$ and Y=O.

23. The compound of claim 20, wherein:
R$^6$ represents H;
C$_{1-4}$-alkyl, saturated or unsaturated, branched or unbranched, mono- or polysubstituted or unsubstituted; or
C(O)O—C$_{1-4}$-alkyl, saturated or unsaturated, branched or unbranched, mono- or polysubstituted or unsubstituted.

24. The compound of claim 20, wherein:
R$^6$ represents H; or
C$_{1-4}$-alkyl, saturated or unsaturated, branched or unbranched, mono- or polysubstituted or unsubstituted.

25. The compound of claim 20, wherein:
R$^6$ represents H, CH$_3$ or C$_2$H$_5$.

26. The compound of claim 20, wherein:
R$^7$ represents C$_{3-8}$-cycloalkyl, aryl or heteroaryl, in each case unsubstituted or mono- or polysubstituted.

27. The compound of claim 20, wherein:
R$^7$ represents cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted.

28. The compound of claim 20, wherein:
R$^7$ represents cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted.

29. The compound of claim 1, wherein said compound is selected from the group consisting of:
4-benzyl-4-dimethylamino-1-phenethylcyclohexanol and the corresponding hydrochloride,
4-dimethylamino-1,4-diphenethylcyclohexanol and the corresponding hydrochloride,
4-benzyl-4-dimethylamino-1-[2-(2-fluorophenyl)ethyl]cyclohexanol and the corresponding hydrochloride,
4-benzyl-4-dimethylamino-1-[2-(4-fluorophenyl)ethyl]cyclohexanol and the corresponding hydrochloride,
4-dimethylamino-4-(2-fluorobenzyl)-1-phenethylcyclohexanol and the corresponding hydrochloride,
4-dimethylamino-4-(3-fluorobenzyl)-1-phenethylcyclohexanol and the corresponding hydrochloride,
4-dimethylamino-4-(4-fluorobenzyl)-1-phenethylcyclohexanol and the corresponding hydrochloride,
4-benzyl-4-dimethylamino-1-[2-(3-fluorophenyl)ethyl]cyclohexanol and the corresponding hydrochloride
4-benzyl-4-dimethylamino-1-(2-fluorobenzyl)cyclohexanol and the corresponding hydrochloride,
4-(allylmethylamino)-4-benzyl-1-phenethylcyclohexanol and the corresponding hydrochloride,
4-benzyl-4-dimethylamino-1-(3-fluorobenzyl)cyclohexanol and the corresponding hydrochloride,
4-benzyl-4-dimethylamino-1-(4-fluorobenzyl)cyclohexanol and the corresponding hydrochloride,
1-benzyl-4-dimethylamino-4-(3-fluorobenzyl)cyclohexanol and the corresponding hydrochloride,
4-benzyl-1-phenethyl-4-pyrrolidin-1-ylcyclohexanol and the corresponding hydrochloride,
4-benzyl-4-dimethylamino-1-(1-methyl-1H-indol-2-yl)cyclohexanol,
1-benzo[b]thiophen-2-yl-4-benzyl-4-dimethylaminocyclohexanol,
1-benzo[b]thiophen-3-yl-4-benzyl-4-dimethylaminocyclohexanol and
1-benzofuran-2-yl-4-benzyl-4-dimethylamino-cyclohexanol.

30. A pharmaceutical composition comprising:
at least one substituted 4-aminocyclohexanol compound according to claim 1 and an auxiliary agent.

31. The pharmaceutical composition of claim 30, wherein said compound is present in the form of a free base.

32. The pharmaceutical composition of claim 30, wherein said compound is present in the form of a pure enantiomer or pure diastereoisomer.

33. The pharmaceutical composition of claim 30, wherein said compound is present in the form of a mixture of stereoisomers.

34. The pharmaceutical composition of claim 30, wherein said compound is present in the form of a racemic mixture.

35. The pharmaceutical composition of claim 30, wherein said compound is present in the form of a solvate.

36. The pharmaceutical composition of claim 30, wherein said compound is present in the form of a hydrate.

37. The pharmaceutical composition of claim 30, further comprising an opioid or an anesthetic.

38. The pharmaceutical composition of claim 37, wherein said opioid is morphine.

39. The pharmaceutical composition of claim 37, wherein said anesthetic is hexobarbital or halothane.

40. A method of alleviating pain selected from the group consisting of acute pain, chronic pain and neuropathic pain in a mammal, said method comprising administering to said mammal an effective pain alleviating amount of a compound according to claim 1 or coadministering to said mammal an effective amount of a compound according to claim 1 with an opioid analgesic or with an anesthetic.

41. A process for producing a substituted 4-aminocyclohexanol compound according to claim 1 comprising the steps of
a. reacting a cyclohexane-1,4-dione, protected with the groups S$^1$ and S$^2$, according to formula II with a cyanide in the presence of a compound of the formula HNR$^{O1}$R$^{O2}$ to give a protected N-substituted 1-amino-4-oxo-cyclohexanecarbonitrile compound corresponding to formula III;

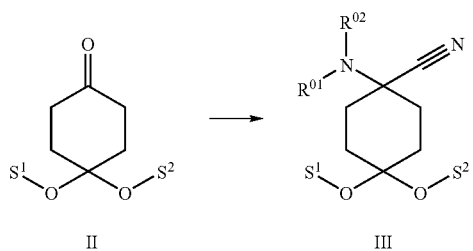

b. reacting the compound according to formula III with organometallic reagents corresponding to the formula metal-R$^3$, so that a compound corresponding to formula IVa is formed;

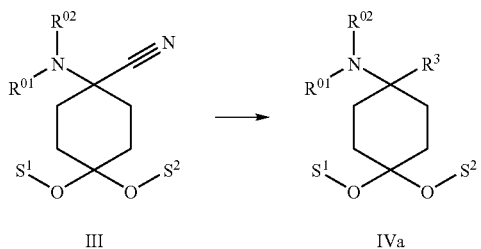

c. removing the protective groups $S^1$ and $S^2$ on the compound corresponding to formula IVa to form a 4-substituted 4-aminocyclohexanone compound corresponding to formula IV;

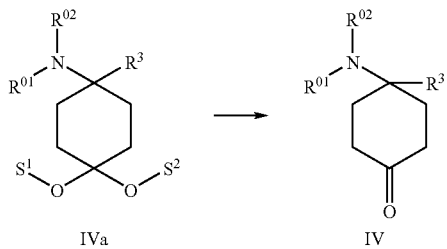

d. reacting the 4-substituted 4-aminocyclohexanone compound corresponding to formula IV with organometallic reagents corresponding to the formula metal-$R^3$ to form compound corresponding to formula V;

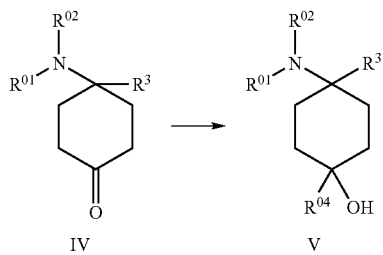

wherein $R^{01}$ and $R^{02}$ independently of one another represent H; H replaced by a protective group; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl bonded via $C_{1-3}$-alkylene and in each case mono- or polysubstituted or unsubstituted;

or $R^{01}$ and $R^{02}$ together form a ring and represent $CH_2CH_2OCH_2CH_2$, $CH_2CH_2NR^{05}CH_2CH_2$ or $(CH_2)_{3-6}$, wherein $R^{05}$ represents H; H replaced by a protective group;

$C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl bonded via $C_{1-3}$-alkylene and in each case mono- or polysubstituted or unsubstituted;

$R^{04}$ represents H; H replaced by a protective group; $C_{3-8}$-cycloalkyl, aryl or heteroaryl, in each case unsubstituted or mono- or polysubstituted; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$, —$C(Y)R^7$, —$C(Y)$—$CH_2R^7$, —$C(Y)$—$CH_2$—$CH_2R^7$ or —$C(Y)$—$CH_2$—$CH_2$—$CH_2R^7$; or —$R^8$-L-$R^9$ wherein Y=O, S or $H_2$;

$R^6$, $R^7$, $R^8$ and $R^9$ have the respective meanings given in claim 1, and $S^1$ and $S^2$ independently of one another represent protective groups or together represent a protective group.

42. The process of claim 41, wherein $S^1$ and $S^2$ together represent a monoacetal group.

43. The process of claim 41, wherein step a) further comprises:

acylating, alkylating or sulfonating the compound corresponding to formula III in any sequence and optionally repeatedly; or where $R^{01}$ and $R^{02}$=H replaced by a protective group, removing at least one protective group and optionally acylating, alkylating or sulfonating the compound corresponding to formula III; or where $R^{01}$ or $R^{02}$=H, introducing at least one protective group and optionally acylating, alkylating or sulfonating the compound corresponding to formula III.

44. The process of claim 41, wherein step b) further comprises:

acylating, alkylating or sulfonating the compound corresponding to formula IVa in any sequence and optionally repeatedly; or where $R^{01}$ or $R^{02}$=H replaced by a protective group, removing at least one protective group and optionally acylating, alkylating or sulfonating the compound corresponding to formula Iva; or where $R^{01}$ or $R^{02}$=H, introducing at least one protective group and optionally acylating, alkylating or sulfonating the compound corresponding to formula IVa.

45. The process of claim 41, wherein step c) further comprises:

acylating, alkylating or sulfonating the compound corresponding to formula IV in any sequence and optionally repeatedly; or where $R^{01}$ or $R^{02}$=H replaced by a protective group, removing at least one protective group and optionally acylating, alkylating or sulfonating the compound corresponding to formula IV; or where $R^{01}$ or $R^{02}$=H, introducing at least one protective group and optionally acylating, alkylating or sulfonating the compound corresponding to formula IV.

46. The process of claim 41, wherein step d) further comprises:

acylating, alkylating or sulfonating the compound corresponding to formula V in any sequence and optionally repeatedly; or where $R^{01}$ or $R^{02}$=H replaced by a protective group, removing at least one protective group and optionally acylating, alkylating or sulfonating the compound corresponding to formula V; or where $R^{01}$ or $R^{02}$=H, introducing at least one protective group and optionally acylating, alkylating or sulfonating the compound corresponding to formula V.

47. The process of claim 41, wherein the protective groups in $R^{01}$, $R^{02}$, $R^{04}$ or $R^{05}$ are selected from the group consisting of alkyl groups, benzyl groups and carbamates.

48. The process of claim 47, wherein the protective groups are selected from the group consisting of fluorenylmethylchloroformate (FMOC), benzyloxycarbonyl (Z) and tert-butyloxycarbonyl (Boc).

49. The process of claim 41, wherein the cyanide of step a) is potassium cyanide.

50. The process of claim 41, wherein the organometallic reagents of step b) are Grignard or organolithium reagents.

51. The process of claim 41, wherein the organometallic reagents of step d) are Grignard or organolithium reagents.

* * * * *